(12) United States Patent
Kosinski et al.

(10) Patent No.: US 8,394,068 B2
(45) Date of Patent: Mar. 12, 2013

(54) FLUSH SYRINGE ASSEMBLY

(75) Inventors: Anthony J. Kosinski, New Providence, NJ (US); Adam Zerda, Oak Ridge, NJ (US); Girum Yemane Tekeste, Hackensack, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 146 days.

(21) Appl. No.: 12/833,432

(22) Filed: Jul. 9, 2010

(65) Prior Publication Data
US 2011/0009829 A1   Jan. 13, 2011

Related U.S. Application Data

(60) Provisional application No. 61/224,688, filed on Jul. 10, 2009.

(51) Int. Cl.
*A61M 5/315*  (2006.01)
*A61M 5/00*   (2006.01)

(52) U.S. Cl. .................. 604/219; 604/210; 604/187

(58) Field of Classification Search .............. 604/187, 604/210, 218–224
See application file for complete search history.

(56) References Cited

U.S. PATENT DOCUMENTS

| | | | |
|---|---|---|---|
| D287,053 S | 12/1986 | Bucchianeri et al. | |
| 5,024,661 A * | 6/1991 | Wender et al. | 604/110 |
| 5,084,017 A * | 1/1992 | Maffetone | 604/110 |
| 5,259,840 A | 11/1993 | Boris | |
| 5,478,311 A | 12/1995 | Klearman | |
| 5,498,243 A | 3/1996 | Vallelunga et al. | |
| D403,762 S | 1/1999 | Gabbard et al. | |
| D420,129 S | 2/2000 | McMahon | |
| D432,231 S | 10/2000 | Balestracci | |
| D437,050 S | 1/2001 | Balestracci | |
| 6,176,846 B1 | 1/2001 | Balestracci | |
| D460,820 S | 7/2002 | Niedospial, Jr. | |
| D461,243 S | 8/2002 | Niedospial, Jr. | |
| 6,530,906 B2 | 3/2003 | Hu | |
| 6,565,529 B1 | 5/2003 | Kimber et al. | |
| 6,790,197 B2 | 9/2004 | Kosinski et al. | |
| 7,276,049 B2 | 10/2007 | Bang et al. | |
| D570,476 S | 6/2008 | Sudo | |
| D575,870 S | 8/2008 | Sudo | |
| 7,686,784 B2 | 3/2010 | Baik | |

(Continued)

FOREIGN PATENT DOCUMENTS

DE  202005004079  7/2006
EP  0627231  12/1994

OTHER PUBLICATIONS

Non-Final Office Action in U.S. Appl. No. 12/833,551, mailed May 25, 2012, 13 pgs.

(Continued)

*Primary Examiner* — Nicholas Lucchesi
*Assistant Examiner* — Rebecca E Eisenberg
(74) *Attorney, Agent, or Firm* — Servilla Whitney LLC

(57) ABSTRACT

Syringe assemblies for use in flush applications are provided. Syringe assemblies according to one aspect of the present invention include a plunger rod and a syringe barrel that incorporate one or more pulsing elements on the plunger rod or barrel that are rotatable to create pulsatile movement or continuous and unimpeded movement a plunger rod within a syringe barrel. One or more embodiments pertain to syringe assemblies permit both pulsatile movement of the plunger rod within the barrel and continuous and unimpeded movement of the plunger rod in the distal direction along substantially the entire length of the syringe barrel upon application of force to the plunger rod in only the distal direction. Methods of flushing a catheter are also provided.

20 Claims, 24 Drawing Sheets

U.S. PATENT DOCUMENTS

| | | |
|---|---|---|
| 2002/0007147 A1 | 1/2002 | Capes et al. |
| 2004/0064105 A1 | 4/2004 | Capes et al. |
| 2004/0087910 A1 | 5/2004 | Nemoto |
| 2004/0186427 A1 | 9/2004 | Pok |
| 2004/0199113 A1 | 10/2004 | Capes et al. |
| 2005/0038385 A1 | 2/2005 | Shen et al. |
| 2005/0148932 A1 | 7/2005 | Rimlinger et al. |
| 2005/0187518 A1 | 8/2005 | Pelkey et al. |
| 2006/0052748 A1 | 3/2006 | Coehlo et al. |
| 2006/0111668 A1 | 5/2006 | Baik |
| 2006/0167409 A1 | 7/2006 | Pelkey et al. |
| 2006/0247582 A1 | 11/2006 | Alheidt et al. |
| 2006/0258983 A1 | 11/2006 | Cirac Sole et al. |
| 2007/0005022 A1 | 1/2007 | Byrne et al. |
| 2007/0073225 A1 | 3/2007 | Lee et al. |
| 2007/0078406 A1 | 4/2007 | Lee |
| 2007/0129674 A1 | 6/2007 | Liversidge |
| 2007/0135764 A1 | 6/2007 | Chen |
| 2007/0179452 A1 | 8/2007 | Kosinski |
| 2007/0299395 A1 | 12/2007 | Pelkey et al. |
| 2008/0021414 A1 | 1/2008 | Alheidt |
| 2008/0221531 A1 | 9/2008 | Alheidt et al. |
| 2008/0262439 A1 | 10/2008 | Alheidt |
| 2008/0300550 A1 | 12/2008 | Schiller et al. |
| 2008/0300551 A1 | 12/2008 | Schiller et al. |
| 2009/0048560 A1 | 2/2009 | Caizza et al. |
| 2009/0062736 A1 | 3/2009 | Jan |
| 2009/0076450 A1 | 3/2009 | Caizza et al. |
| 2009/0093793 A1 | 4/2009 | Gross et al. |
| 2009/0171285 A1 | 7/2009 | Wang |
| 2009/0177156 A1 | 7/2009 | MacLean |
| 2009/0287161 A1 | 11/2009 | Traub et al. |
| 2009/0318880 A1 | 12/2009 | Janish |
| 2010/0076370 A1 | 3/2010 | Howlett et al. |
| 2010/0174236 A1 | 7/2010 | Burns et al. |
| 2010/0274190 A1 | 10/2010 | Wayman et al. |
| 2010/0286609 A1 | 11/2010 | Mahurkar |
| 2010/0286610 A1 | 11/2010 | Chang |

OTHER PUBLICATIONS

"International Search Report of PCT/US2010/041559", mailed on Oct. 1, 2010, 6 pages.

"IPRP and Written Opinion of PCT/US2010/041559", dated Jan. 10, 2012, 11 pages.

\* cited by examiner

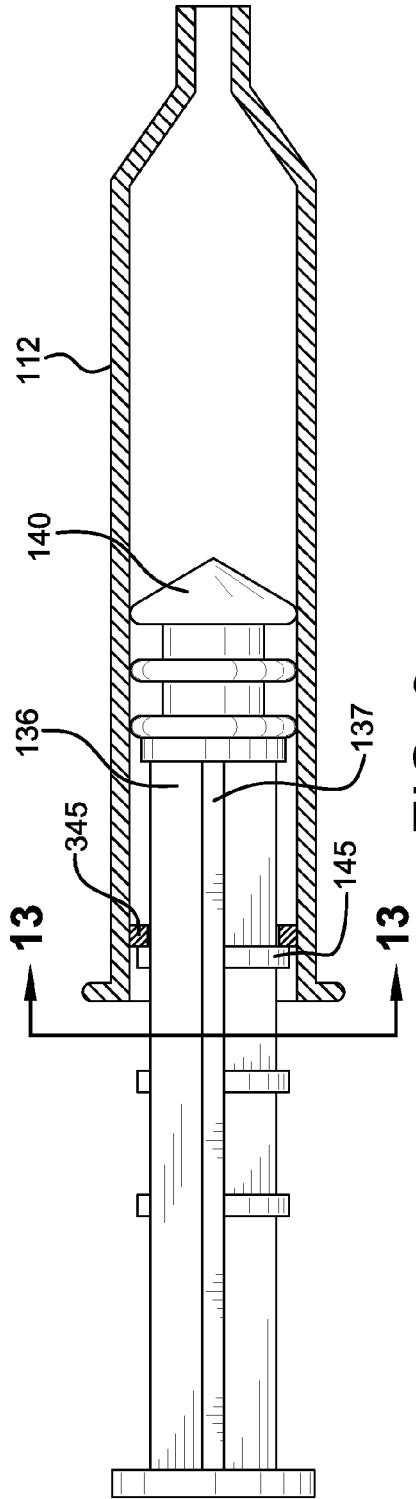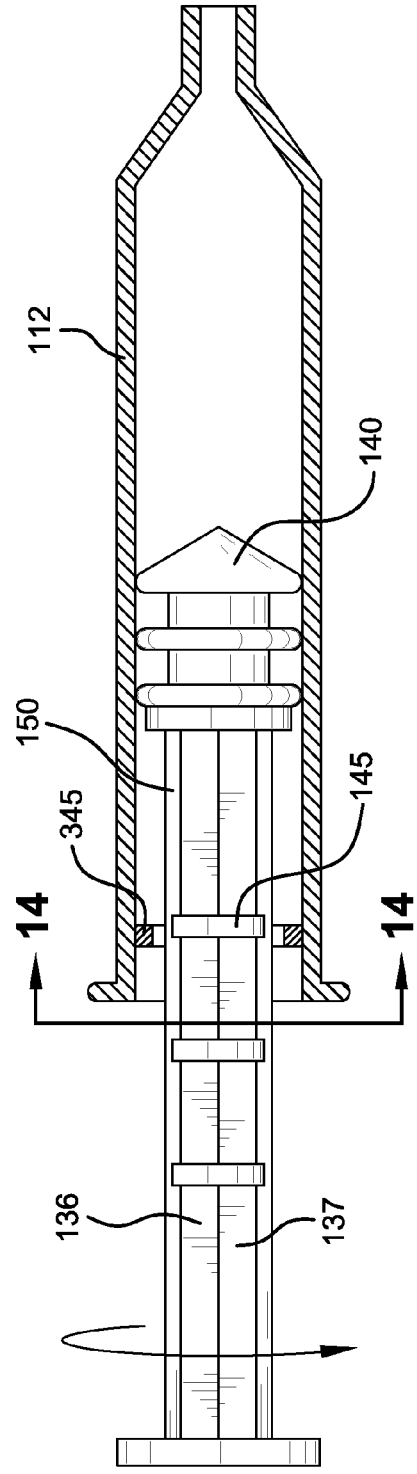

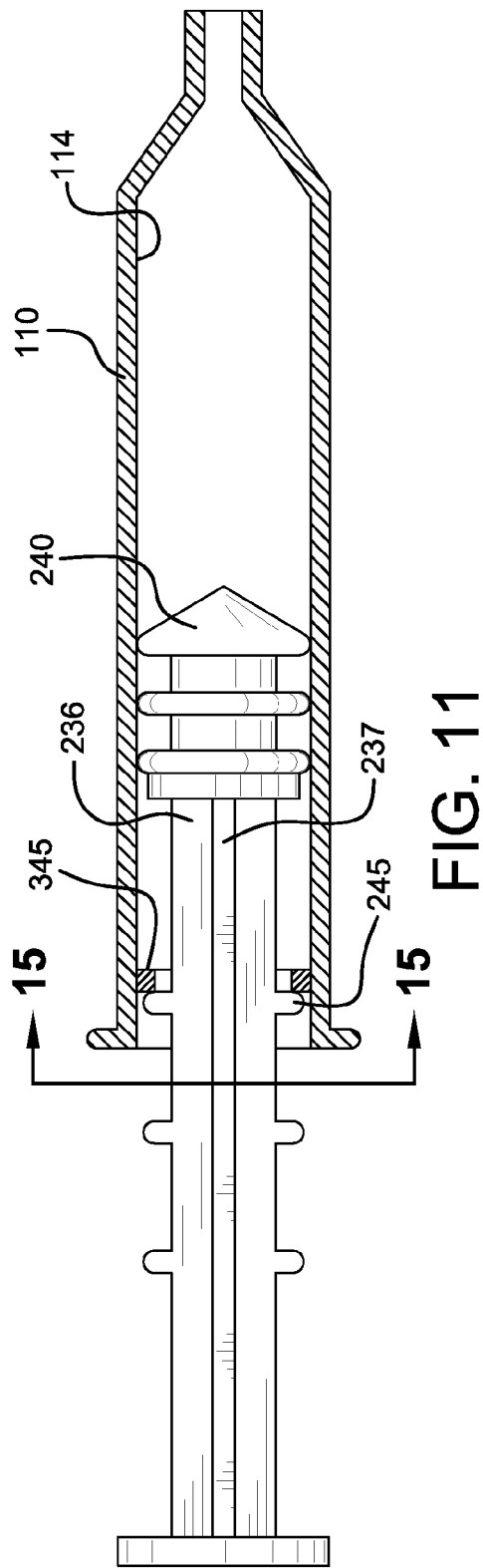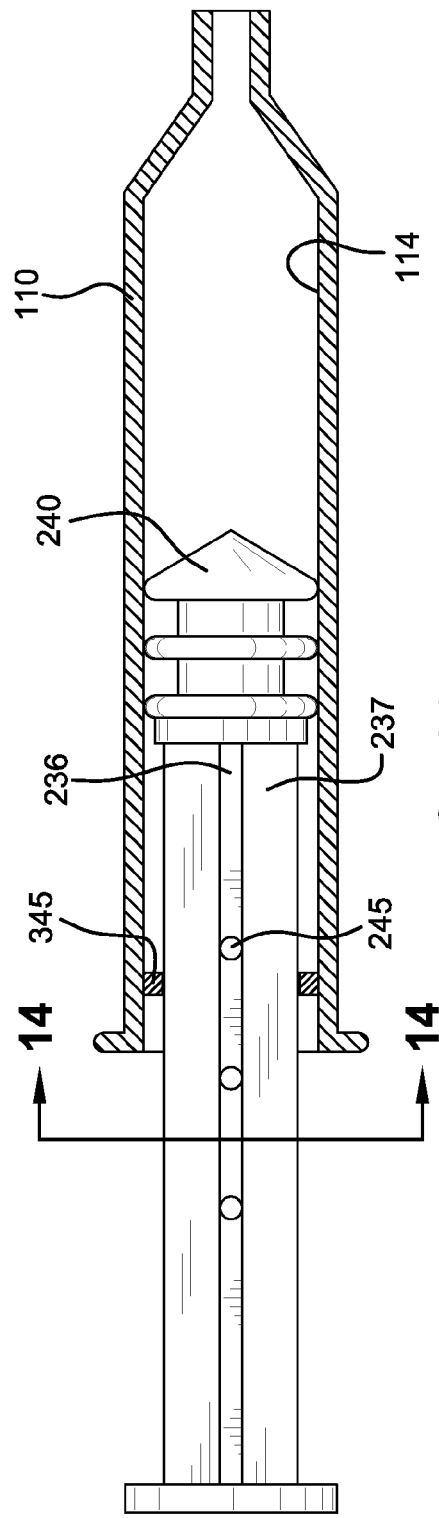

FLUSH SYRINGE ASSEMBLY

TECHNICAL FIELD

The present invention relates to syringe assemblies and particularly to, syringe assemblies for use in flush procedures for vascular access devices (VAD's).

BACKGROUND

VAD's are commonly used therapeutic devices and include IV catheters. There are two general classifications of VAD's, peripheral catheters and central venous catheters. If not properly maintained, VAD's can become occluded. To ensure VAD's are used properly and do not become occluded, standards of practice have been developed. These standards include a cleaning procedure, which is commonly referred to as a flush procedure or flushing a catheter.

VAD standards of practice usually recommend flush procedures be performed after catheter placement, before fluid infusion, and before and after drug administration, blood sampling, transfusions and parenteral nutrition. The goal of these flush procedures is to confirm catheter patency, avoid drug incompatibilities, ensure the complete drug dose administration, prevent thrombus formation and minimize the risk of blood stream infections. Flush procedures require different types and amounts of flush solutions. The most commonly used flush solutions are saline and or heparin lock solution. The type of flush solution and amount vary depending on the specific type of catheter. Flush solution volumes between 5 and 10 ml are most common but can range from 1 ml to 20 ml.

For flush procedures, an I.V. line refers to a system containing a VAD, a tubing set with clamp and may terminate with a port or valve. The most common types of ports are covered by pierceable septums or pre-slit septums and are known in the art and sometimes referred to as "PRN" from the Latin pro re nata meaning "as the need arises". The septum is preferably made of rubber or another elastomeric material, which permits insertion of a sharp needle cannula in order to infuse fluids or to withdraw fluids from the catheter. Upon withdrawal of the needle cannula the septum seals itself. Ports having pre-slit septums are used with blunt cannula or the frusto-conically shaped tip of a syringe barrel. The syringe tip or the blunt cannula (which is usually attached to a syringe) is gently pushed through the pre-slit septum to establish fluid communication.

I.V. valves, another type of terminal I.V. access device that does not require a needle having a sharp tip, are activated by the frusto-conically shaped tip of a syringe barrel to allow fluid communication between the interior of the syringe and the catheter. These valves may contain features for delivering fluid from a storage compartment in the valve to the catheter, and are referred to in the art as positive displacement valves. Such a valve is taught in U.S. Pat. No. 6,206,861.

Flush procedures may be enhanced by use of a "push-pulse" (also referred to as "start-stop" or "push-pause") technique to remove debris or residue in the catheter that may cause occlusion or other undesirable effects. The removal of debris or residue is referred to a purging and prevents the build-up of deposits of blood, blood residue and IV drugs within a catheter or other VAD device. Such build-up can cause partial or complete blockage of the fluid pathway in a catheter system, require expensive and potentially dangerous methods for purging the affected catheter or a total catheter exchange. Often, such blockages lead to interruptions in therapy that may compromise patient care. The build-up of residue within a catheter can also increase infection risk by providing a breeding medium for microorganisms. For this reason, push-pulse is traditionally taught to healthcare workers.

As is understood by one skilled in the art, the push-pulse flushing technique introduces or creates turbulence within the syringe barrel when uneven pressure or force is applied to the plunger rod in the distal direction as the distal end of the plunger rod moves toward the barrel wall during expulsion. In this disclosure, a convention is followed wherein the distal end of the device is the end closest to a patient and the proximal end of the device is the end away from the patient and closest to a practitioner. When such techniques are used in conjunction with catheters, turbulence is introduced within the catheter. Turbulent or pulsing flow causes a swirling effect that moves any debris or residue attached to the catheter. Turbulent or pulsing flow can be provided in a relatively controlled manner by a syringe that includes a plunger rod that interacts with the syringe barrel as the plunger rod is pushed forward to automatically create sharp pulses in fluid flow and pressure. In contrast to push-pulse and controlled pulsatile flow, conventional or "smooth" (also referred to as "straight" or "laminar") flushing techniques require the application of substantially constant pressure or force to the plunger rod in the distal direction. Conventional or smooth flushing techniques may also include the application of pressure or force that increases or decreases substantially linearly to the plunger rod in the distal direction. However, the use of features that provide the force differential that creates turbulent or pulsing fluid flow generally cannot be applied with infusion pumps or other delivery systems that require slow and controlled delivery of medication to patients. For example, certain infusion pumps have high pressure alarms and the forces and/or pressures created by push-pulse techniques of flushing can set off the high pressure alarm.

There is a need for a flush syringe assembly that can be used with both manual IV therapies and therapies that use infusion pumps.

SUMMARY

The present invention is directed to a syringe assembly for use in flush applications. Syringe assemblies according to a first aspect of the present invention include a plunger rod and a syringe barrel that have that permit continuous and unimpeded movement of the plunger rod with respect to the barrel and pulsatile movement of a plunger rod in the distal direction within a syringe barrel. The syringe assemblies described herein also provide to the user the ability to select between pulsatile or continuous and unimpeded movement of the plunger rod within the barrel. The features providing pulsatile movement allows the user to substantially achieve the effects of a push-pulse flushing techniques that impart turbulence to the flow of the flush solution into the catheter or other medical device connected to the flush syringe. The features for providing continuous and unimpeded movement allows the user to utilize smooth flushing techniques that do not actively change or increase turbulence in the flow of the flush solution into a catheter or other medical device. The range of the pulsatile movements and continuous and unimpeded movements is described more fully below.

In one or more embodiments, the pulsatile or continuous and unimpeded movement of the plunger rod is provided by one or pulsing more elements disposed on the plunger rod and/or syringe barrel that are complementary and may be configured or arranged to substantially achieve the effects of a push-pulse flushing technique when expelling the contents of the barrel, while also being capable of alternatively permitting conventional or smooth flushing techniques. The selection of flushing techniques may be tailored by the user to a specific application or specific needs of a patient. Indicia may also be provided on the plunger rod and/or syringe barrel that provides visual indication of whether the plunger rod and syringe barrel assembly is configured for pulsatile movement to create pulses or rapid and intentional variations in fluid flow and/or pressure or continuous and unimpeded movement causing conventional or smooth flushing in which fluid flow and/or pressure are substantially constant with little variation or spiking in pressure.

As used herein, the term "pulsatile movement" shall include plunger rod motion caused by variations in the pressure or force applied to the plunger rod. In the embodiments described herein, the variations in the pressure of force applied to the plunger rod are caused by the physical barrier provided by the interactions between the one or more pulsing elements disposed on the plunger rod and/or barrel that must be overcome to permit the plunger rod to advance in the distal direction within the barrel. The delay in the movement of the plunger rod caused by the interaction of the one or more pulsing elements disposed on the plunger rod and/or the one or more pulsing elements disposed on the barrel and the movement of the one or more pulsing elements of the plunger rod past the one or more pulsing elements on the barrel upon application of a force on the plunger rod yields the force necessary to provide pulsatile movement and turbulent or pulsing flushing fluid pressure. These changes pressure or force impart turbulence to the flush solution as it is expelled into a catheter or other medical device . . . . The variations in pressure or force may increase or decrease and such changes may occur cyclically or acyclically. The variations in pressure or force may further be modified to increase or decrease by pre-defined amounts. As will be described herein, the variations in pressure or force are created by changes in mechanical interference between the plunger rod and the barrel as the plunger rod slides distally and proximally within the barrel upon application of force to the plunger rod in only the distal direction. As used herein, the term "interference" shall be used interchangeably with the phrase "mechanical interference or force" and includes friction, frictional interference or frictional force. The variations in pressure or force applied to the plunger rod results in rapid changes in fluid pressure, which can result in pressure spikes having a duration of less than about two seconds or less than about one second. During each spike duration, the pressure varies from a low pressure value of less than about 10 psi or less than about 5 psi, suddenly increases to a high value of up to 25 psi and rapidly decreases down to a low pressure value of less than about 20 psi, 18 psi, 16 psi, 14 psi, 12 psi, 10 psi or about 5 psi. According to certain embodiments the pressure spikes are substantially equal, meaning that the variation between the high value of the spikes is less than about 10 psi or about 5 psi. It will be understood that the high value of pressure can be tailored to specific applications by modifying the shape of the features disposed on the plunger rod and/or syringe barrel.

As used herein, the phrase "continuous and unimpeded movement" shall include movements caused by a substantially constant pressure or force applied to the plunger rod as the plunger rod moves from the most proximal position within the barrel to the most distal position within the barrel, namely, when the distal face of the stopper is in contact with the distal wall of the barrel. Continuous and unimpeded movement may also include movements caused by increases in pressure or force that are substantially linear, distinguished from rapid spikes in pressure in which the pressure suddenly increases and decreases in less than about two seconds. The constant or linearly increasing pressure or force applied to the plunger rod is caused by the lack of changes in mechanical interference between the plunger rod as it moves within the barrel. It will be understood that the changes or lack of changes in mechanical interference may occur as the plunger rod slides distally and/or proximally within the barrel. Such applications of force or pressure to the plunger rod are utilizes in techniques that are known as straight flushing, smooth flushing or laminar flushing.

Both continuous and unimpeded movement and pulsatile movement occur as the stopper on the plunger rod are disposed at the proximal end of the barrel and moved in the distal direction along the substantially the entire length of the barrel, until the plunger rod reaches the distal wall of the syringe. Stated in other terms, continuous and unimpeded movement and pulsatile movement also occur as the user applies pressure or force on the plunger rod in the distal direction to expel the entire contents of the barrel. In other words, continuous and unimpeded movement and pulsatile movement occur in a single stroke of the plunger rod as it moves distally within the barrel from the proximal most point of the barrel to the distal most point of the barrel.

The manual push-pulse flushing technique is recognized as useful for reducing the risk of infections that may be caused by the presence of debris or residue, including blood and/or drug residue, that is not purged or removed from catheters and other similar medical devices and may enhance microbial growth. The use of structural elements or pulsing elements that provide or cause pulsatile movement, as described herein, eliminates human error or deviations from standard practices that may arise from requiring manual or user initiated use of the manual push-pulse flushing technique. Further, the incorporation of structural elements or pulsing elements that provide or cause continuous and unimpeded movement in the same syringe assembly allows the user flexibility to change the flow of the flush solution to pulsing or continuous or non-pulsing flow without having to switch assemblies without having to switch assemblies. Control over the pressure of the flush solution being expelled is a specific problem to flush syringe assemblies. For flushing techniques, the flush solution must have a pressure that is high enough and must have the turbulent or pulsing flow necessary to remove debris and residue, but the pressure must not be too high to cause overpressurization of catheters or other medical devices. The structural elements or pulsing elements disclosed herein also provide greater control over the flush pressure or the pressure of the flush solution as it is being expelled than manual push-pulse flushing techniques. The user does not need to manually vary the amount of force applied to the plunger rod to ensure turbulent or pulsing flow, thus eliminating the possibility that the flush solution has a fluid pressure that is too great. In addition, the pulsing elements described herein are shaped and sized so that movement of the plunger rod within the barrel in a pulsatile manner is controlled so the flush solution being expelled has a fluid pressure that solution does not exceed levels that could overpressurize the catheter and interfere with normal catheter use, but also has the turbulent or pulsing flow required to remove debris and reside from catheters and other medical devices.

In accordance with one aspect of the present invention, a flush syringe assembly is provided having a barrel and an elongate plunger rod disposed within the barrel and capable of sliding in the proximal and distal direction. The plunger rod and the barrel or portions of the barrel include one or more pulsing elements that, when aligned, increase mechanical interference between the plunger rod and barrel.

In one or more embodiments, the plunger rod is rotatable within the barrel to create pulsatile movement or to create continuous and unimpeded movement of the plunger rod within the barrel. In one or more variants, the barrel is rotatable with respect to the plunger rod to create pulsatile movement or to create continuous and unimpeded movement of the plunger rod within the barrel. Optionally, the barrel may include a rotating body that rotates with respect to the plunger rod and the barrel to create pulsatile movement or to create continuous and unimpeded movement of the plunger rod within the barrel.

In one or more embodiments, the barrel includes an open proximal end, a distal end and a side wall that defines an inside surface extending from the proximal end to the distal end. The inside surface of the barrel defines a chamber for retaining fluid, such as flush solution. The distal end of the barrel includes a distal wall and a tip extending distally from the distal wall. The tip includes a passageway therethrough in fluid communication with the chamber. The plunger rod of one or more embodiments includes a proximal portion or end, a distal portion or end and a body portion having an outside surface extending from the proximal end to the distal end. The proximal end of the plunger rod may include a thumb press. A stopper with a distal face may be provided on the distal end having a distal face. In one embodiment, the syringe assembly includes one or more pulsing elements disposed on at least one of the plunger rod or the barrel that provide increase mechanical interference between the plunger rod and barrel as the plunger rod moves distally and/or proximally within the barrel. In one variation, the one or more pulsing elements are rotatable to create pulsatile movement or continuous and unimpeded movement of the plunger rod within the barrel or, in other words, to allow the user to select pulsatile movement or continuous and unimpeded movement of the plunger rod within the barrel. In a specific configuration, the pulsatile or continuous and unimpeded fluid movement occur as the plunger rod is moved within the barrel from the open proximal end of the barrel to the distal wall of the barrel.

In one or more embodiments, the one or more pulsing elements are disposed on the plunger rod and/or the insides surface of the barrel. In accordance with one or more embodiments, the one or more pulsing elements may include a plurality of extensions disposed on the outside surface of the plunger rod. The extensions of one or more embodiments may extend radially outwardly toward the inside surface of the barrel. Alternatively, the one or more pulsing elements may include a plurality of protrusions disposed on the inside surface of the barrel. The protrusions may extend radially inwardly toward the outside surface of the plunger rod. In one or more embodiments, a portion of the outside surface of the plunger rod is free of extensions and a portion of the inside surface of the barrel is free of protrusions.

According to one or more embodiments, the one or more pulsing elements includes at least one extension disposed on the outside surface of the plunger rod, at least one protrusion disposed on the inside surface of the barrel, such that the at least one extension cooperating with the at least one protrusion to increase the mechanical forces to advance the plunger rod distally into the barrel from the open proximal end of the barrel to the distal wall of the barrel. In a specific embodiment, the at least one extension extends radially outwardly toward the inside surface of the barrel and the at least one protrusion extending radially inwardly toward the outside surface of the plunger rod. In a more specific embodiment, the one or more pulsing elements comprises a plurality of extensions disposed on the outside surface of the plunger rod and a plurality of protrusions disposed on the inside surface of the barrel. In an even more specific embodiment, a portion of the outside surface of the plunger rod is free of extensions and a portion of the inside surface of the barrel is free of protrusions, despite the presence of at least one extension and protrusion on the plunger rod and barrel.

According to one or more embodiments, the movement of the plunger rod in the distal direction creates interference with the barrel, which is varied upon alignment of the plurality of extensions or the at least one extension and the plurality of protrusions or the at least one protrusion. In one or more embodiments, the alignment of the plurality of protrusions or the at least one protrusion and the plurality of extensions or the at least one extension results in variations in the interference between the plunger rod and the barrel that requires an increase in mechanical force to overcome the interference. In one or more embodiments, the alignment of the features for providing continuous and unimpeded fluid movement and features for providing pulsatile movement results in no variations in the interference between the plunger rod and barrel. In other words, alignment of the plurality of extensions or the at least one extension disposed on the plunger rod with the portion of the barrel that is free of protrusions results in no variations in the interference between the plunger rod and the barrel. In addition, the alignment of the plurality of protrusions or the at least one protrusion of the barrel with the portion of the plunger rod that is free of extensions results in no variations in the interference between the plunger rod and the barrel.

In one or more embodiments, the one or more pulsing elements may also include a pulsing element disposed at the proximal end of the barrel. The pulsing element may be provided as a separate piece attached to a barrel. The barrel may be free of protrusions or other features for providing pulsatile movement of the plunger rod. The pulsing element includes an inside surface that defines an opening with at least one projection that extends inwardly into the opening. The pulsing element may be utilized in embodiments in which the plunger rod includes at least one extension or a plurality of extensions disposed on the outside surface thereof and that extend radially outwardly toward the inside surface of the syringe barrel. The pulsing element may be rotatable and may be rotated such that the at least one projection engages with the at least one extension or a plurality of extensions disposed on the plunger rod to cause variations in the interference between the plunger rod and the barrel. The variations in the interference may be sufficient be caused by the interactions between the protrusions and the extensions disposed on the plunger rod that require an increased mechanical force to be applied to advance the plunger rod distally into the barrel from the open proximal end of the barrel to the distal wall of the barrel.

In one or more embodiments, a portion of the pulsing element may be free of projections. The plunger rod utilized with the pulsing element may also include a portion of its outside surface that is free of extensions. The pulsing element may be rotatable with respect to the plunger rod to create pulsatile movement or continuous and unimpeded movement of the plunger rod within the barrel. Specifically, the pulsing element may be rotated while the plunger rod and remaining portions of the barrel remain in a fixed position with respect to each other. To create pulsatile movement of the plunger rod or variations in the interference between the plunger rod and barrel, the pulsing element may be rotated to align the at least one extension of the plunger rod and the at least one projection of the pulsing element. In one or more embodiments, the pulsing element may be rotated such that the at least one extension of the plunger rod is aligned with the portion of the inside surface of the pulsing element that is free of projections. In such configurations, this alignment of the pulsing element and the plunger rod result in no variations in the interference between the plunger rod and barrel and allow continuous or unimpeded movement of the plunger rod within the barrel.

A second aspect of the present invention pertains to a flush syringe assembly having a barrel and a plunger rod disposed within the barrel, as described herein, wherein the barrel and plunger rod are cooperatively configured to permit both pulsatile movement of the plunger rod within the barrel and continuous and unimpeded movement of the plunger rod in the distal direction along substantially the entire length of the syringe barrel upon application of force to the plunger rod in only the distal direction. Stated in other terms, the syringe assembly is capable of pulsatile movement or continuous and unimpeded movement as the plunger rod moves in only the distal direction along substantially the entire length of the syringe barrel. In a specific embodiment, the syringe assembly includes a plunger rod that is rotatably disposed within the barrel to permit selection of pulsatile movement or continuous and uninterrupted movement. In a more specific configuration, a portion of the barrel may be rotatable around the plunger rod to permit selection of pulsatile movement or continuous and uninterrupted movement.

A third aspect of the present invention pertains to a method of flushing a catheter. In one or more embodiment, the method includes attaching a flush syringe assembly, as described herein, to a catheter, wherein the chamber of the flush syringe assembly contains a preselected amount of flush solution in the chamber. The method includes selecting the manner of moving the plunger rod within the barrel from one of a pulsatile manner and a continuous and unimpeded manner. In other words, selecting whether to purge the syringe barrel or simply expel the contents of the flush syringe assembly either pulsatile movement or continuous or unimpeded movement. The method also includes applying a force in the distal direction to the plunger rod until a desired amount of flush solution is expelled. In one or more embodiments, the method may also include changing the manner of moving the plunger rod within the barrel from one of the pulsatile manner and the continuous and unimpeded manner to the other of the pulsatile manner and the continuous or unimpeded manner. In other words, the user may change the manner in which the plunger rod is moving within the barrel. For example, if the user selects moving the plunger rod in the pulsatile manner and begins expelling the flush solution, the user may change their mind and switch the manner in which the plunger rod is moving to a continuous or unimpeded manner, or vice versa.

BRIEF DESCRIPTION OF THE DRAWINGS

FIG. 9 illustrates a partial cross-sectional view of the plunger rod of FIG. 1 inserted into the barrel shown in FIG. 7;

FIG. 10 illustrates a partial cross-sectional view of the plunger rod of FIG. 2 inserted into the barrel shown in FIG. 7;

FIG. 11 illustrates a partial cross-sectional view of the plunger rod of FIG. 4 inserted into the barrel shown in FIG. 7;

FIG. 12 illustrates a partial cross-sectional view of the plunger rod of FIG. 5 inserted into the barrel shown in FIG. 7;

DETAILED DESCRIPTION

Figure 1:
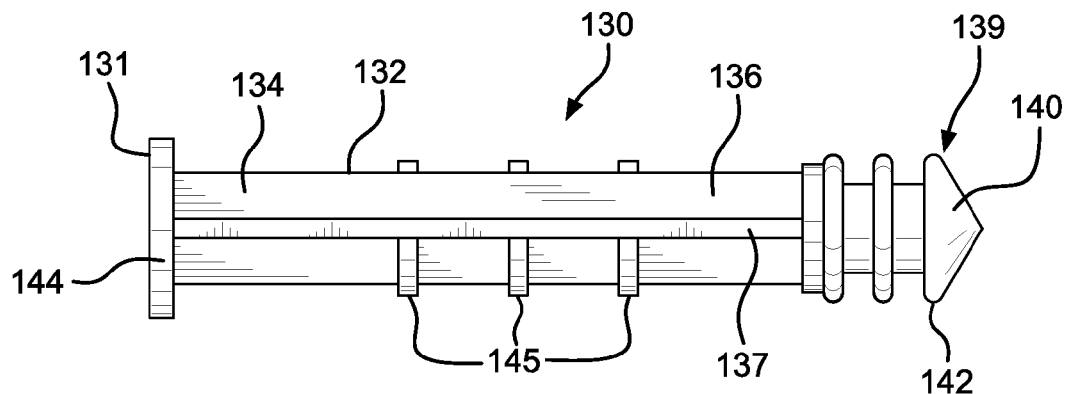
FIG. 1 illustrates a side-elevational view of the plunger rod according to one or more embodiments of the present invention.

Before describing several exemplary embodiments of the invention, it is to be understood that the invention is not limited to the details of construction or process steps set forth in the following description. The invention is capable of other embodiments and of being practiced or being carried out in various ways.

Syringe assemblies according to a first aspect include a plunger rod and a syringe barrel that incorporate an element for providing continuous and unimpeded movement and an element for providing pulsatile movement of a plunger rod in the distal direction within a syringe barrel. The assembled syringe is shown in FIGS. 9-16, with the components separately shown in FIGS. 1-8. Referring to FIGS. 1-16, a syringe assembly according to one embodiment comprises a barrel 110 including a side wall 112 having an inside surface 114 defining a chamber 116 for retaining fluid, an open proximal end 111 and a distal end 119 including a distal wall 118 with a tip 115 extending distally therefrom. The tip 115 includes a passageway 113 therethrough in fluid communication with the chamber 116. The open proximal end 111 includes finger flanges 120. The side wall 112 of the barrel may be cylindrical or may have another shape.

The tip 115 of the barrel may include a luer slip connection (not shown) or a locking luer type collar (not shown) concentrically surrounding tip 115. The collar (not shown) may include an inside surface having at least one thread thereon. A needle assembly (not shown) including a cannula having a proximal end, a distal end, and a lumen therethrough may also optionally be provided. A hub (not shown) having an open proximal end containing a cavity and a distal end may be attached to the proximal end of the cannula so that the lumen is in fluid communication with the cavity of the hub. The needle assembly (not shown) is removably attached to the tip of the barrel through engagement of the tip to the cavity of the hub so that the lumen is in fluid communication with the chamber of the barrel. The chamber 116 of the barrel may include a desired amount of flush solution. The side wall 112 may include measuring indicia (not shown) to indicate the amount of flush solution contained within the chamber 116.

A plunger rod 130 is provided and includes an elongate body portion 132 having a proximal end 131, and a distal end 139. The plunger rod 130 is slidably within the chamber 115 of the barrel 110 for driving fluid out of the chamber 116. The elongate body portion 132 of the plunger rod extends outwardly from the open proximal end 111 of the barrel and may be disposed within the chamber 116. The plunger rod 130 includes a thumb press 144 at the proximal end 131 and a stopper 140 at the distal end 139. The stopper 140 includes a sealing edge 142 that forms a seal with the inside surface 114 of the barrel. The shape of the plunger rod may be modified to fit within barrels with side walls having different shapes.

The stopper 140 of one or more embodiments may be integrally formed on the distal end 139 of the plunger rod or may form a separate component that is connected to the distal end 139 of the plunger rod. The distal end 139 of the plunger rod may include an integrally formed stopper (not shown). The stopper 140 may include a conically-shaped distal surface and the barrel may include a conically-shaped inside surface at its distal wall. The stopper 140 is slidably positioned in fluid-tight engagement with the inside surface 114 of the barrel for drawing fluid into and driving fluid out of the chamber. If the syringe assembly is prefilled from the manufacturer, the stopper need not be used for or able to draw fluid into the barrel.

The stopper 140 may be made of any material suitable for providing a seal with the inside surface 114 of the barrel. For example, the stopper 140 may be made of thermoplastic elastomers, natural rubber, synthetic rubber or thermoplastic materials and combinations thereof. The stopper 140 may be integrally formed or composed of separate components of the same or different materials joined together. The plunger rod 130 may be made of material which is more rigid than the stopper such as polypropylene, polyethylene and the like. Materials should be chosen to be compatible with the procedure being used.

Figure 2:
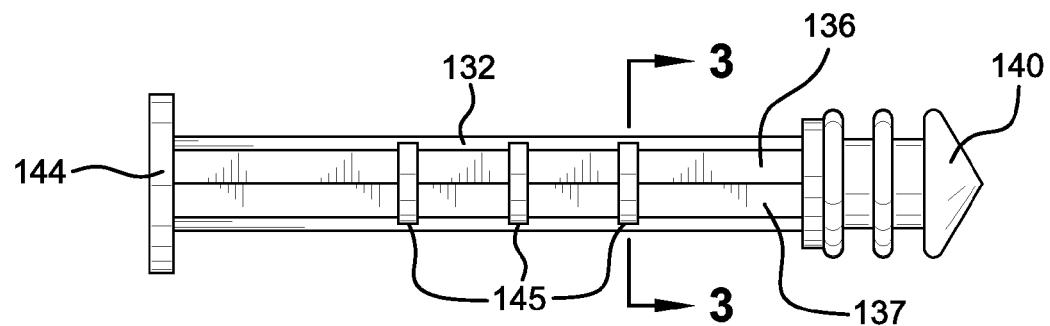
FIG. 2 shows a side-elevational view of FIG. 1 rotated 90° clockwise or counterclockwise.
Figure 3:
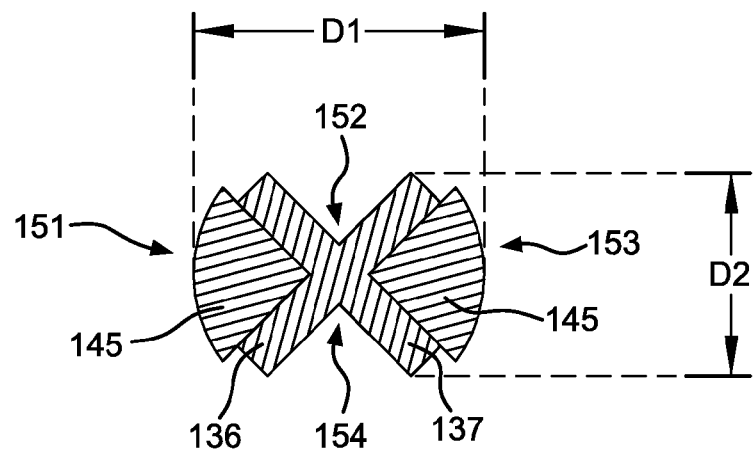
FIG. 3 illustrates a partial cross-sectional view of FIG. 2 taken along line 3-3.
Figure 1A:
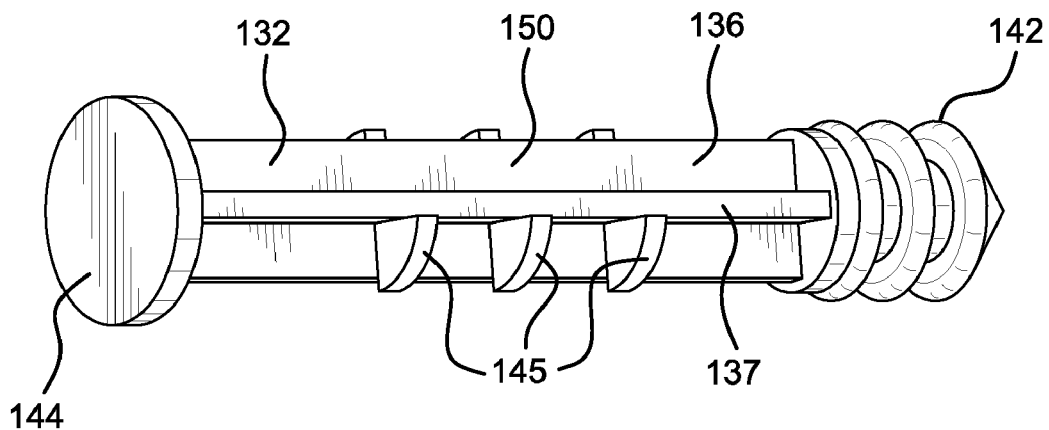
FIG. 1A is a perspective view of the plunger rod shown in FIG. 1.

The elongate body portion 132 of the plunger rod includes an outside surface 134, forming a perimeter around the body portion 132 and an axial length extending from the proximal end 131 to the distal end 139. The body portion 132 may include a single beam or features, which may have cylindrical or other shapes. As shown in FIGS. 1-3, the body portion 132 may be formed by two perpendicularly intersecting beams 136, 137. The beams may have a rectangular cross-section. In the embodiment shown, the two intersecting beams 136, 137 intersect to form an outside surface outlining four quadrants 151, 152, 153, 154 (shown more clearly in FIG. 5) that face the inside surface 114 of the barrel and extend along the axial length from the proximal end 131 to the distal end 139 of the plunger rod.

In the embodiments shown in FIGS. 1-6, one or more pulsing elements are disposed on the outside surface of the body portion 132 of the plunger rod and on the inside surface 114 of the barrel. The pulsing elements may be integrally formed or provided as separate components that may be added to the plunger rod and/or barrel. The plunger rod 130 or barrel 110 may further include features for the attachment of separate pulsing elements. In accordance with the embodiments shown in FIGS. 1-3, the one or more pulsing elements are provided as a plurality of extensions in the shape of a disc 145 or rib members. In such embodiments, the discs 145 are disposed on the outside surface of the body portion 132 of the plunger rod. In embodiments where the body portion 132 includes two intersecting beams 136, 137, the discs 145 may be connected to the adjacent beams 136, 137 and extend radially outwardly toward the inside surface 114 of the barrel from a quadrant. In the embodiment shown, the discs 145 are formed in two non-adjacent quadrants 151, 153 and are connected to beams 136, 137. In embodiments where the body portion 132 includes a single beam, the disc 145 may be peripherally formed along a segment or portion of the outside surface 134 of the plunger rod 130 and extend radially outwardly toward the inside surface 114 of the barrel. The outside surface 134 of the plunger rod may include segments or portions that are free of discs 150 or other extensions. In a specific embodiment, two discs may be formed peripherally along two opposite segments of the outside surface of the plunger rod, leaving two opposite segments of the outside surface of the plunger rod that are free of discs. The discs 145 may be positioned at regular intervals along the length of the plunger rod. In one or more alternative embodiments, the discs 145 may be positioned at irregular intervals and/or may be positioned at or adjacent to the proximal end 131 or the distal end 139 of the plunger rod.

Figure 4A:
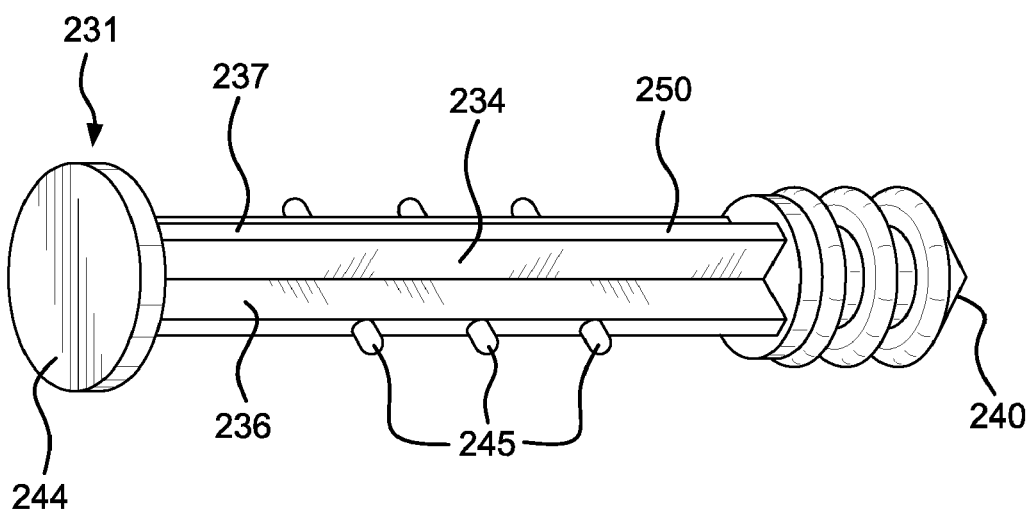
FIG. 4A is a perspective view of the plunger rod shown in FIG. 1.
Figure 4:
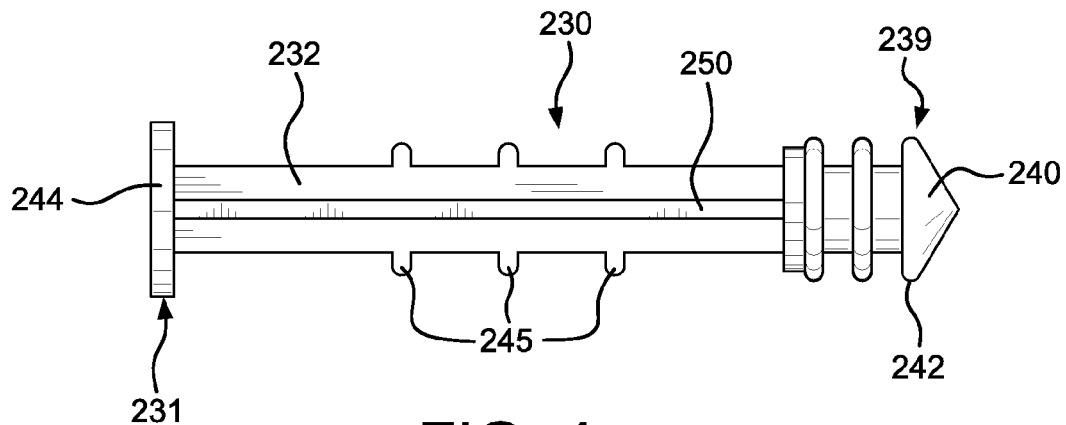
FIG. 4 illustrates a side-elevational view of an alternative embodiment of the plunger rod shown in FIG. 1.
Figure 5:
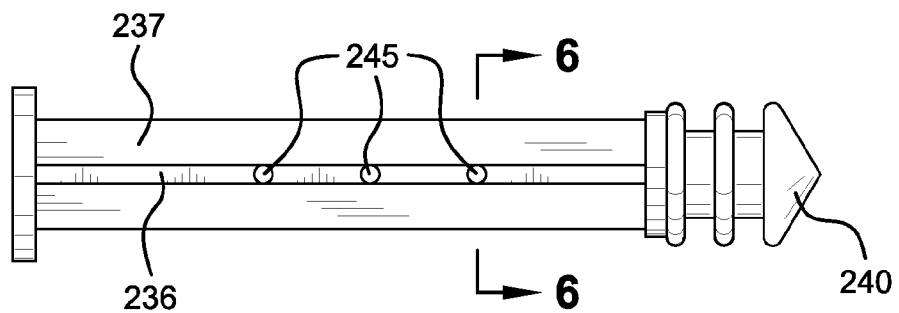
FIG. 5 illustrates a side-elevational view of FIG. 4 rotated 90° clockwise or counterclockwise.
Figure 6:
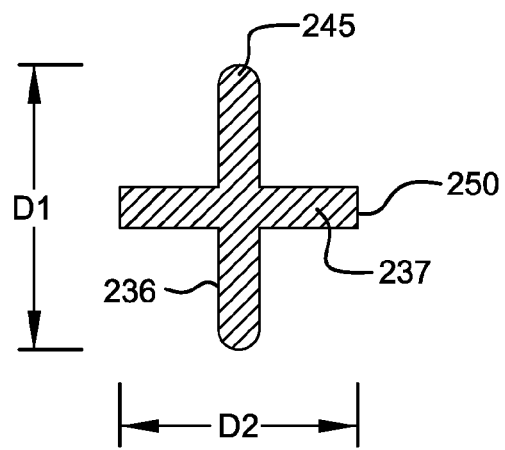
FIG. 6 shows a partial cross-sectional view of the FIG. 5 taken along line 6-6.

FIGS. 4-6 illustrate an alternative embodiment of the plunger rod 230. Plunger rod 230 includes a proximal end 231 and a distal end 239 with an elongate body portion 232 extending from the proximal end 231 to the distal end 239. The distal end 239 of the plunger rod 230 includes a stopper 240 with a sealing edge 242 and the proximal end 239 includes a thumb press 244. The elongate body portion 232 of the plunger rod includes an outside surface 234, forming a perimeter around the body portion, and an axial length extending from the proximal end 231 to the distal end 239. In the embodiment shown, body portion 232 is formed by two perpendicularly intersecting beams 236, 237. The beams may have a rectangular cross-section. In the embodiment shown in FIGS. 4-6, the one or more pulsing elements are provided in the form of protrusions 245 disposed on the outside surface of the plunger rod 230. The one or more protrusions 245 radiate outwardly toward the inside surface 214 of the barrel. The one or more protrusions 245 are limited to a portion of the perimeter of the body portion of the plunger rod, leaving the remaining portion 250 of the perimeter of the plunger rod free of protrusions or extensions. As shown in FIGS. 4-6, a plurality of protrusions 245 may be disposed along the axial length of the plunger rod and may be disposed at pre-defined intervals along the axial length. In a specific embodiment, the pre-defined intervals are equally spaced.

In embodiments utilizing two perpendicularly intersecting beams 236, 237 the protrusions 245 may be disposed at opposite ends of one beam, as shown in FIG. 6. In embodiments utilizing a single beam to form a body portion, one or more protrusions 245 may be peripherally formed along a segment of the outside surface 234 of the plunger rod, while the remaining segments of the outside surface are free of any protrusions 245 or other extensions. In a specific embodiment, the protrusions may also be formed peripherally along two opposite segments of the outside surface 234 of the plunger rod, leaving two opposite segments of the outside surface 234 of the plunger rod that are free of protrusions. The protrusions 245 may be positioned at regular intervals along the length of the plunger rod. In one or more alternative embodiments, the protrusions 245 may be positioned at irregular intervals and/or may be positioned at or adjacent to the proximal end 231 or the distal end 239 of the plunger rod.

The one or more pulsing elements may also be disposed on the inside surface of the barrel. In the embodiment shown in FIGS. 7-8, the elements are provided in the form of a retaining ring 345 disposed on the inside surface 114 of the barrel 110 and extending radially inwardly toward the chamber and/or a plunger rod. The retaining ring 345 interacts with the pulsing elements disposed on the plunger rod, for example the discs 145 and/or the protrusions 245, to provide pulsatile movement of the plunger rod 130 as it moves distally within the barrel. In such embodiments, the retaining ring 345 forms a narrowed cross-sectional width in comparison to the cross-sectional width formed by the inside surface 114 of the barrel. The retaining ring 345 and may include at least one opening 350 that defines an expanded cross-sectional portion that has a larger cross-section than the retaining ring. The inside surface 114 of the barrel has a smaller cross-sectional width at the retaining ring 345 than at the opening 350. The at least one opening 350 forms a portion of the inside surface of the barrel that is free of any extensions and does not interact with the plunger rod. In a specific embodiment, two or more retaining rings 345 may be disposed along pre-defined intervals along the length of the inside surface 114 of the barrel. Alternative embodiments may include two retaining rings and two openings on each ring, three retaining rings and two openings on each ring, three retaining rings and three openings, and other combinations of retaining rings and openings. It will be understood that the elements disposed on the inside surface of the barrel and outside surface of the plunger rod can be formed to cooperate with each other. In an even more specific embodiment, the pre-determined intervals, at which the retaining rings are disposed, are regularly spaced along the length of the inside surface of the barrel or, alternatively, are irregularly spaced along the length of the inside surface of the barrel.

According to an alternative embodiment, the one or more pulsing elements formed at discrete points, instead of being formed peripherally along the inside surface of the barrel. Such embodiments include portions of the inside surface 114 of the barrel that are free of pulsing elements and that do not interact with the plunger rod 130. Such discrete elements may be disposed at pre-defined intervals along the length of the inside surface of the barrel and, in an even more specific embodiment, the pre-determined intervals are equally spaced along length of the inside surface of the barrel.

During use, the user aligns the extensions and/or projections of the plunger rod and the syringe barrel, respectively, to select the desired movement. For example, if pulsatile movement is desired, the user rotates the plunger rod and/or syringe barrel so that the one or more pulsing elements disposed on the plunger rod interact with the one or more pulsing elements disposed on the inside surface of the barrel or the pulsing element provided to the barrel as a separate component (which are described below in more detail). Where continuous and unimpeded movement is desired, such as the movement resulting from the smooth flushing technique, the user rotates the plunger rod and/or syringe barrel so that the one or more pulsing elements disposed on the plunger rod do not interact with the one or more pulsing elements disposed on the barrel.

With specific reference to FIG. 9, to provide pulsatile movement to the plunger rod 130, the discs 145 are aligned with the retaining ring 345 such that there is interaction between the discs 145 and the retaining ring 345 when a force is applied to the plunger rod in the distal direction to expel the flush solution contained within the barrel. With reference FIG. 11, the protrusions 245 of plunger rod 230 are aligned with the retaining ring 345 of the syringe barrel such that there is interaction between the protrusions 245 and the retaining ring 345 when a force is applied to the plunger rod in the distal direction to expel the flush solution contained within the barrel.

In one or more embodiments, the one or more pulsing elements may be provided as a separate component for use with a syringe barrel. The separate one or more pulsing element may be utilized with standard syringe barrels that do not include any features for providing pulsatile movement with the plunger rods described herein or otherwise. Such syringe barrels may be free of any internal projections, such as the retaining ring 345 described above.

Figure 22:
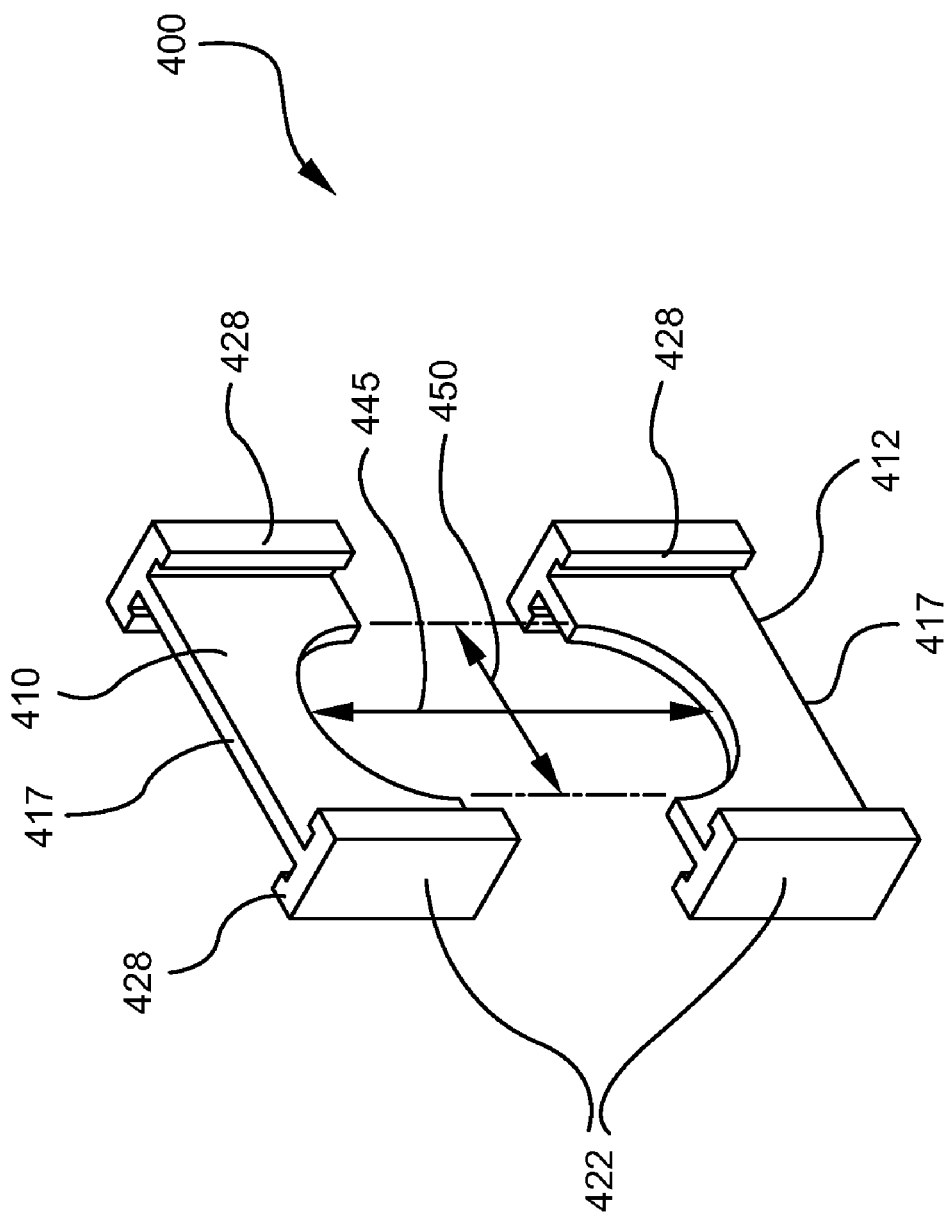
FIG. 22 illustrates a perspective view of the first pulsing element shown in FIG. 18.
Figure 23:
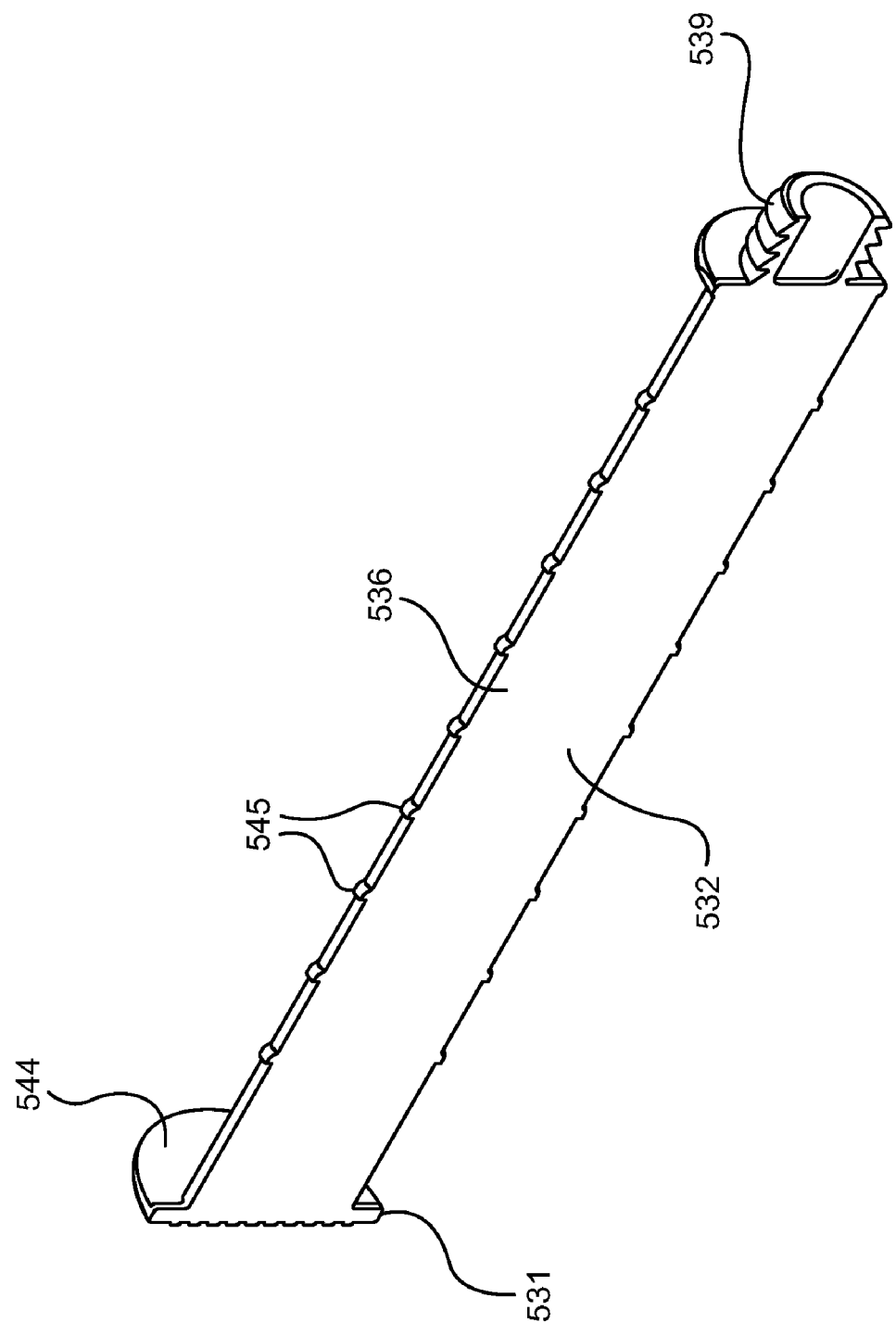
FIG. 23 illustrates a perspective cross-sectional view of the plunger rod shown in FIG. 1.

FIGS. 17-28 illustrate a first pulsing element 400 that may be disposed on an open proximal end of a syringe barrel. Specifically, first pulsing element 400 includes an upper portion 410 and a lower portion 412 that join to attach to the open proximal end of a syringe barrel. In the embodiment shown, the upper portion 410 and the lower portion 412 form a shell or partial enclosure around an open proximal end of the syringe barrel. The first pulsing element 400 includes an opening that surrounds the syringe barrel, as will be described herein. In the embodiment shown, the upper portion 410 and the lower portion 412 are identical. It will be understood, however, that the upper portion 410 and the lower portion 412 may also be different from one another. The upper portion 410 and the lower portion 412 include a shell wall 414 that that is disposed perpendicularly to the syringe barrel. The shell wall 414 includes a distal side 415 and a proximal side 416. The shell wall also includes a top end 417, a bottom end 418, a first end 419 and a second end 420, as shown in FIG. 22. The upper portion 410 and the lower portion 412 also include two side walls 422 that are disposed at the first end 419 and the second end 420 of the shell wall 414. The side walls 422 include a distal side 424, a proximal side 426, and at least one nesting element 428 that forms a rim or retaining wall for securing the first pulsing element 400 to a proximal end of the syringe barrel. In the embodiment shown, the pulsing element 400 includes two nesting elements 428 that are disposed on distal side 424 and the proximal side 426 of both of the side walls 422. The nesting element 428 in the embodiment shown in FIG. 22 includes an L shaped wall that extends inwardly toward the opening of the pulsing element 400.

As more clearly shown in FIG. 22, the shell wall 414 includes a partial opening 430 at the bottom end 418. When the upper portion 410 and the lower portion 412 are joined around the proximal end of a syringe barrel, the partial opening 430 of the upper portion 410 and the partial opening 430 of the lower portion 412 form a full opening 432 that receives a plunger rod and surrounds the open proximal end of the barrel. The full opening 432 has a smaller cross-sectional width portion 445 when measured from the bottom end 418 of the upper portion 410 to the bottom end of the lower portion 412. The smaller cross-sectional portion 445 is less than the cross-sectional width of the plunger rods described herein when measured at the one or more pulsing elements disposed on the plunger rods. The full opening 432 has a greater cross-sectional width portion 450 when measured from the joints of the upper portion 410 and the bottom portion 412 that is greater than the cross-sectional width of the plunger rods described herein when measured at the one or more pulsing elements disposed on the plunger rods. The interaction between the bottom ends 418 of the full opening 434 formed by the upper portion 410 and the lower portion 412 and the one or more pulsing elements of the plunger rods described herein cause the plunger rod to provide pulsatile movement of the plunger rod as the plunger rod moves distally within the barrel.

As shown in FIGS. 17-28, the first pulsing element 400 is utilized with a syringe barrel 510 and a plunger rod 530. The syringe barrel 510 includes an open proximal end 511, a distal end 519, and a side wall 512 that extends from the distal end 519 to the proximal end 511. The side wall 512 includes an inside surface 514 that defines a chamber 516 for retaining fluid. The distal end 519 includes a distal wall 518 with a tip 515 extending distally therefrom. The tip 515 includes a passageway 517 therethrough in fluid communication with the chamber 516. The tip 515 may include a tip cap 513 attached thereto. The open proximal end 511 includes finger flanges 520. The side wall 512 of the barrel may be cylindrical or may have another shape and is free of any features that project into the chamber.

Figure 17:
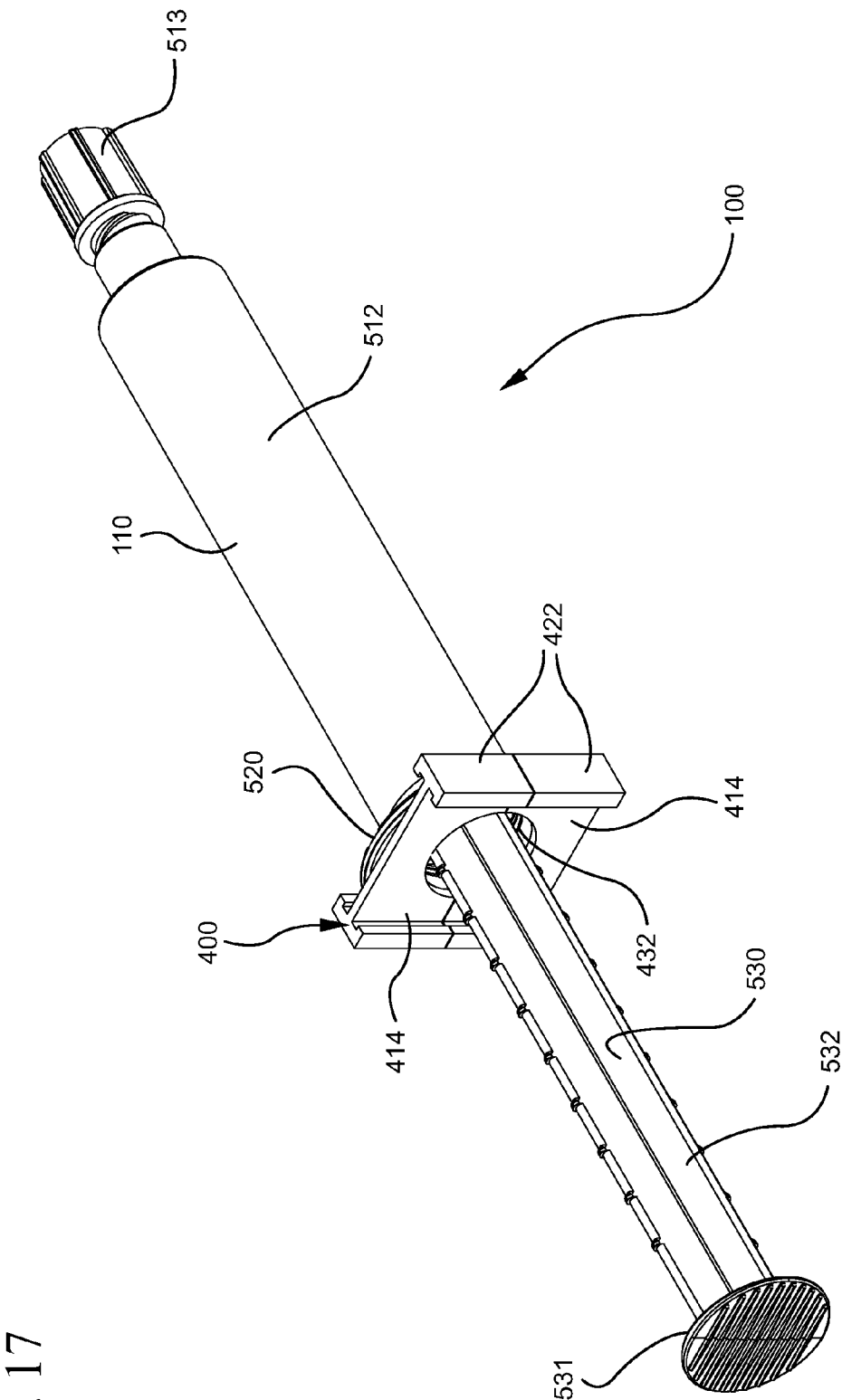
FIG. 17 illustrates a perspective view of a first pulsing element assembled with a flush syringe assembly that includes a syringe barrel and a plunger rod.

To assemble the pulsing element 400 to the syringe barrel 510, the upper portion 410 and the lower portion 412 are joined around the finger flanges 520. Specifically, the finger flange 520 is inserted into the nesting element 428 of the upper portion 410 and the lower portion 412 as the upper portion 410 and the lower portion 412 are joined or brought in contact or near contact with each other. The upper portion 410 and the lower portion 412 are attached to the finger flanges 520 by friction interference fit, as shown in FIG. 17. It will be understood that other attachment mechanisms can be used, for example, snap fit, cooperating channels, adhesive attachment and the like.

The plunger rod 530 shown in FIGS. 17-20 includes a proximal end 531 and a distal end 539 with an elongate body portion 532 extending from the proximal end 531 to the distal end 539. The distal end 539 of the plunger rod 530 includes a stopper 540 with a sealing edge 542 and the proximal end 531 includes a thumb press 544. The elongate body portion 532 of the plunger rod includes an outside surface 534, forming a perimeter around the body portion, and an axial length extending from the proximal end 531 to the distal end 539. In the embodiment shown, body portion 532 is formed by two perpendicularly intersecting beams 536, 537. The beams may have a rectangular cross-section. In the embodiment shown in FIGS. 18-20, the one or more pulsing elements are provided in the form of protrusions 545 disposed on the outside surface of the plunger rod 530. The one or more protrusions 545 extend outwardly toward the inside surface of the barrel. In the embodiment shown, the protrusions 545 form half-circles or partial ribs on one end of the beam 536.

Figure 18:
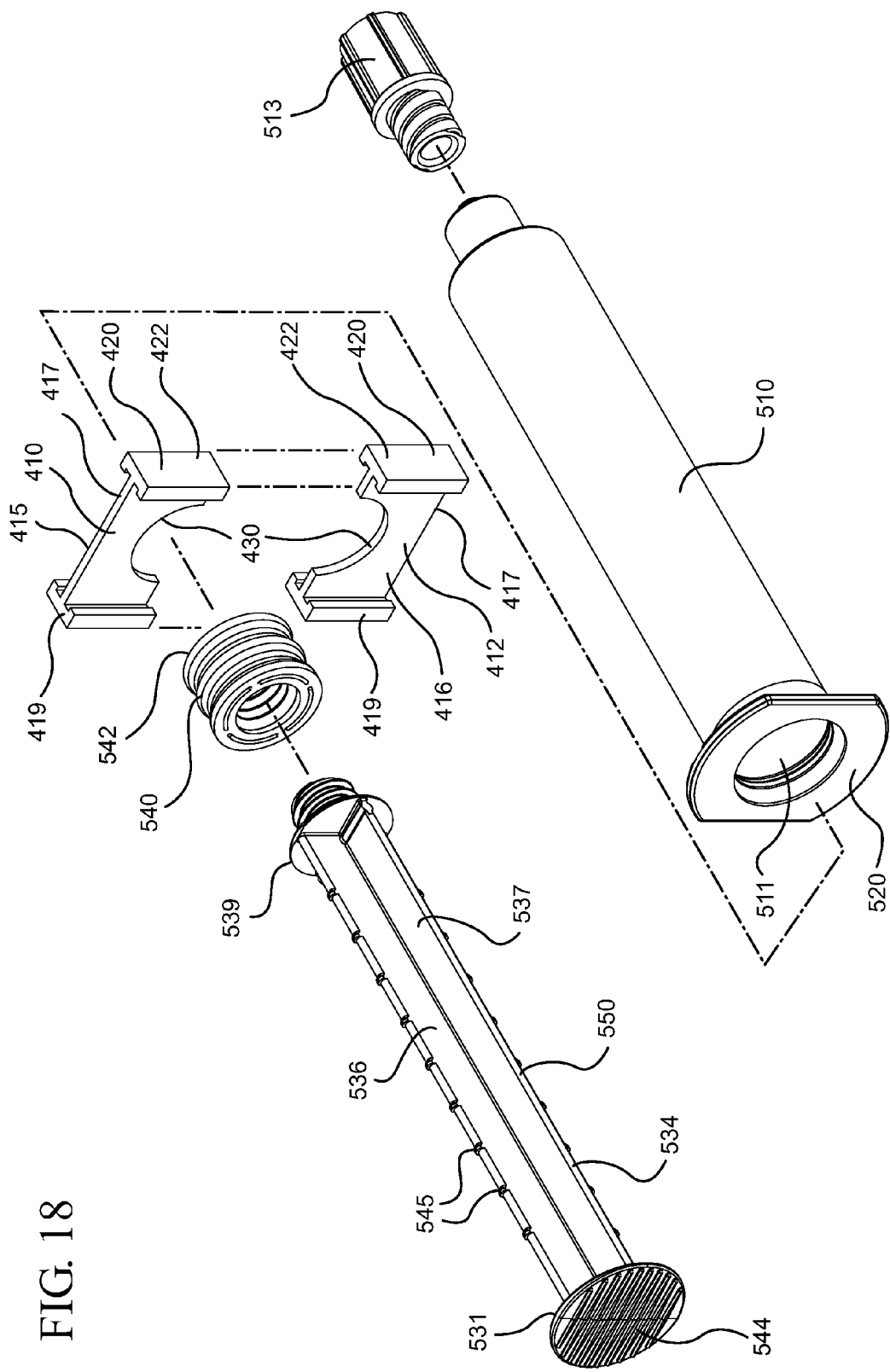
FIG. 18 illustrates an exploded view of the first pulsing element and the flush syringe assembly shown in FIG. 17.
Figure 19:
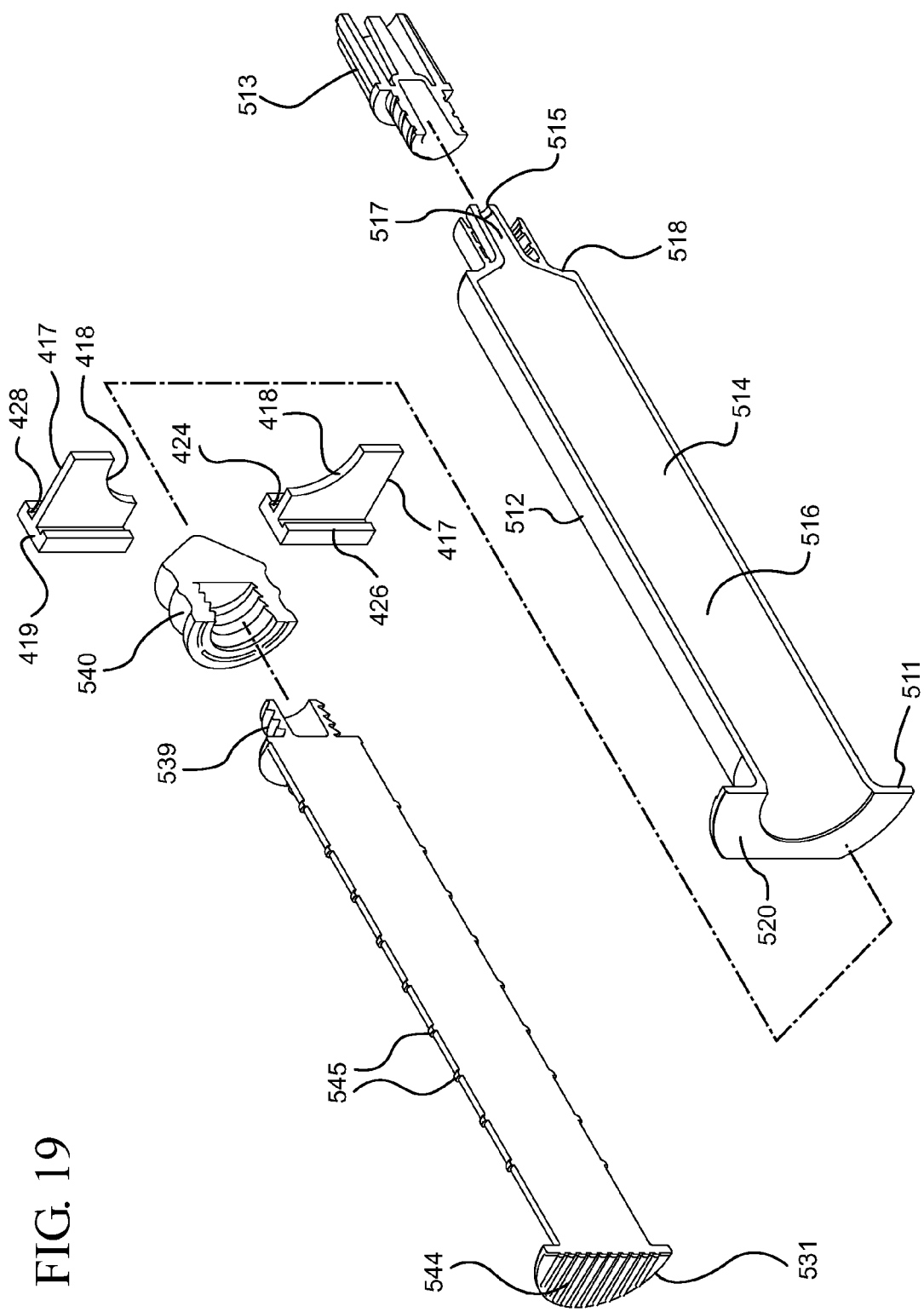
FIG. 19 illustrates a cross-sectional view of the first pulsing element, and the flush syringe assembly shown in FIG. 18.
Figure 20:
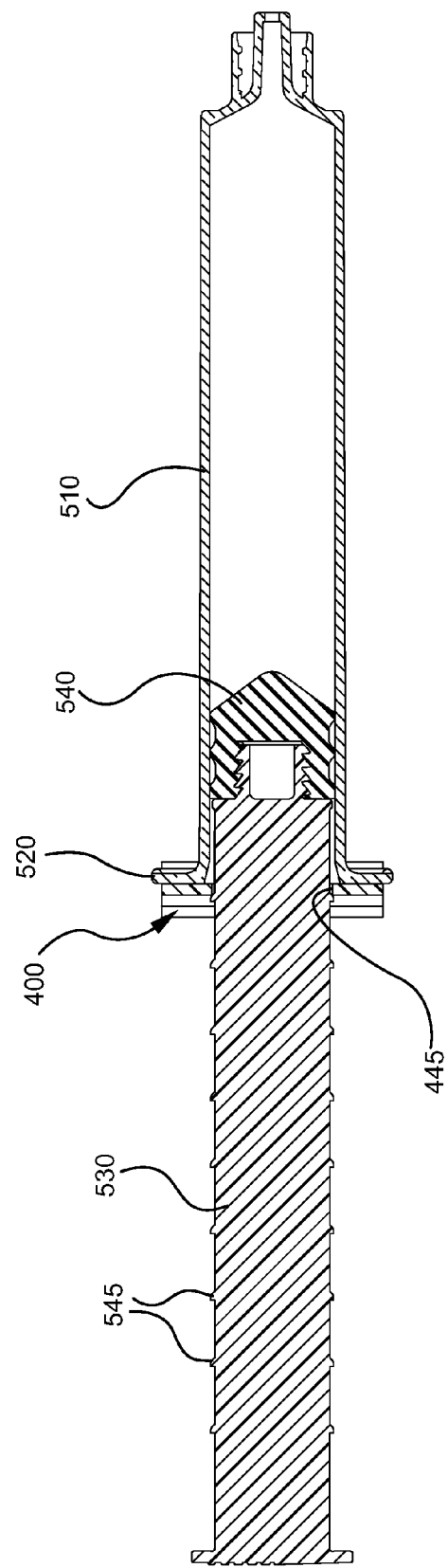
FIG. 20 illustrate a side cross-sectional view of the first pulsing element and the flush syringe assembly shown in FIG. 17.
Figure 21:
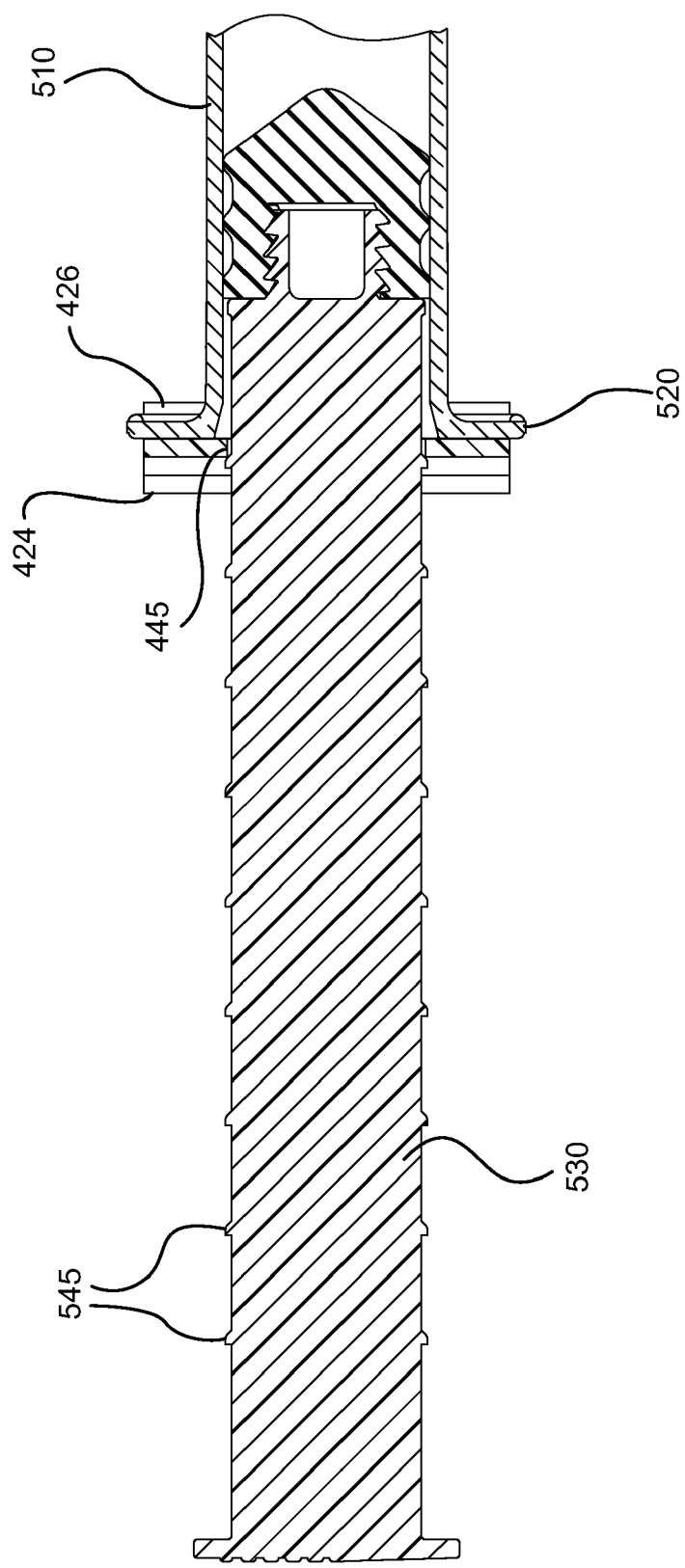
FIG. 21 illustrates an enlarged view of the first pulsing element and the flush syringe assembly shown in FIG. 20.

The one or more protrusions 545 are limited to a portion of the perimeter of the body portion of the plunger rod, leaving the remaining portion 550 of the perimeter of the plunger rod free of protrusions. Specifically, the protrusion 545 is disposed on opposite ends of beam 536 while the opposite ends of beam 537 are free of any protrusions and are indicated as portions of the plunger rod that are free of any protrusions 550. As shown in FIGS. 18-20, a plurality of protrusions 545 may be disposed along the axial length of the plunger rod and may be disposed at pre-defined intervals along the axial length. In a specific embodiment, the pre-defined intervals are equally spaced.

In embodiments utilizing a single beam to form a body portion, one or more protrusions 545 may be peripherally formed along a segment of the outside surface 534 of the plunger rod, while the remaining segments of the outside surface are free of any protrusions 545 or other extensions. In a specific embodiment, the protrusions may also be formed peripherally along two opposite segments of the outside surface 534 of the plunger rod, leaving two opposite segments of the outside surface 534 of the plunger rod that are free of protrusions. The protrusions 545 may be positioned at regular intervals along the length of the plunger rod. In one or more alternative embodiments, the protrusions 545 may be positioned at irregular intervals and/or may be positioned at or adjacent to the proximal end 531 or the distal end 539 of the plunger rod.

Figure 24:
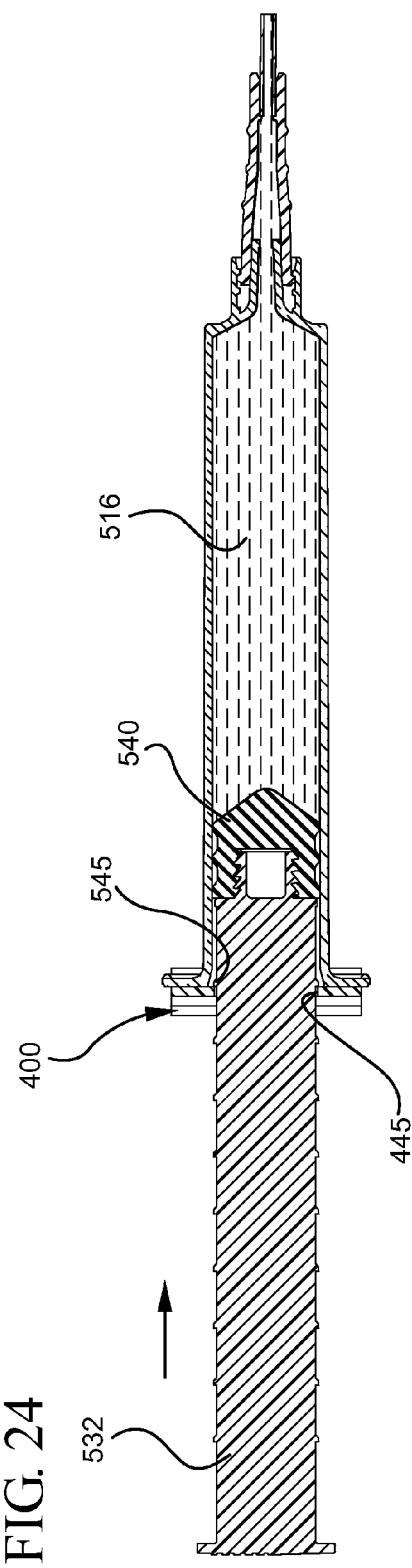
FIG. 24 illustrates the first pulsing element and the flush syringe assembly shown in FIG. 20 after application of a force in the distal direction on the plunger rod.
Figure 24A:
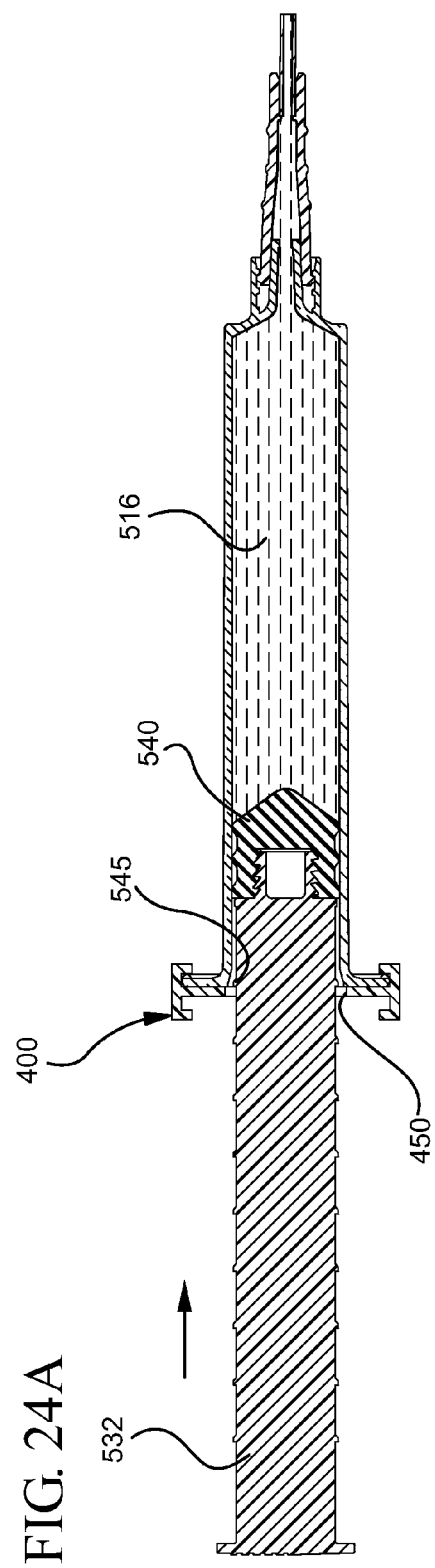
FIG. 24A illustrates the first pulsing element and the flush syringe assembly shown in FIG. 24 after rotation of the first pulsing element.
Figure 25:
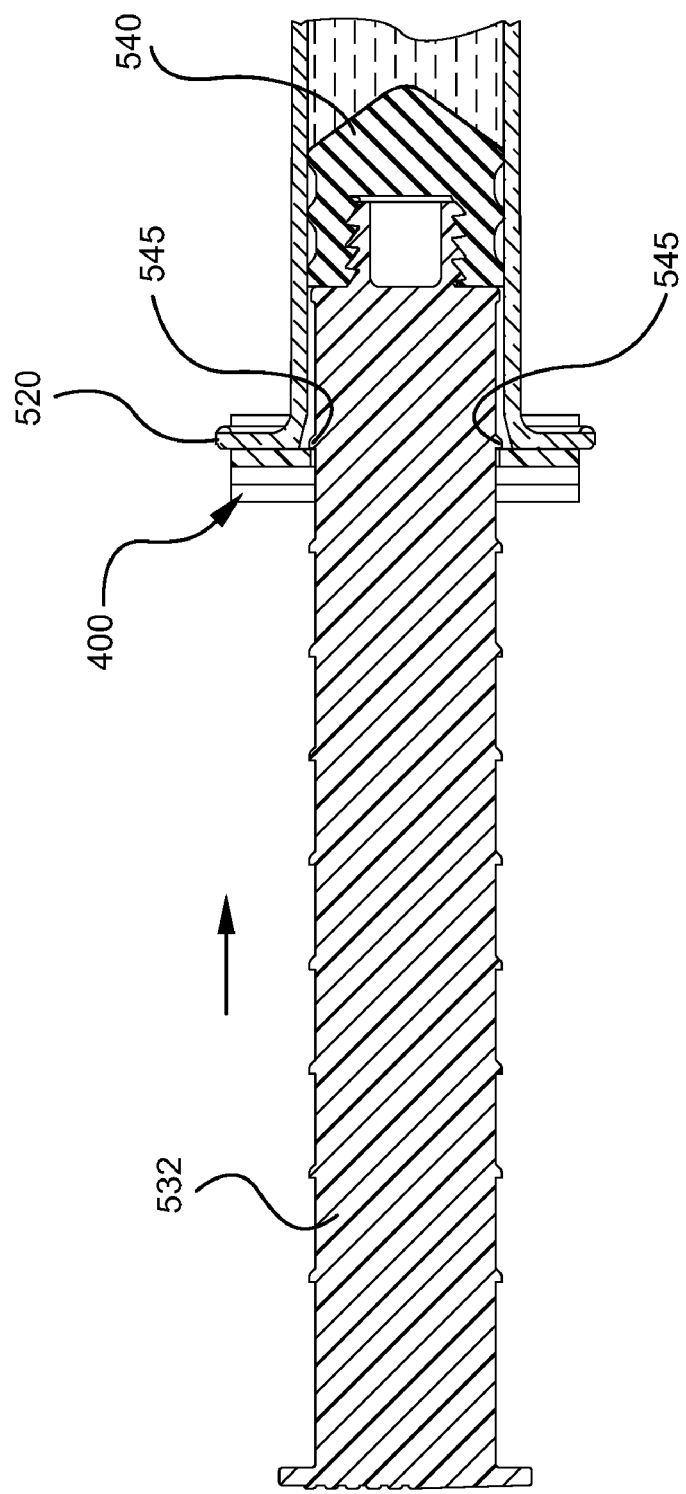
FIG. 25 illustrates an enlarged view of the first pulsing element and the flush syringe assembly shown in FIG. 24.

In use, the plunger rod 530 is inserted into the chamber 516 of the syringe barrel 510 through the full opening 434 of the first pulsing element 400. The protrusions 545 of the plunger rod may be aligned with smaller cross-sectional width 554 of the full opening 432 to provide pulsatile movement to the plunger rod. The user may rotate the plunger rod 530 such that the protrusions 545 are aligned with the larger cross-sectional width portion 450 of the full opening 532 to provide continuous and unimpeded movement of the plunger rod, as shown in FIG. 24A.

The upper portion 410 and the lower portion 412 of first pulsing element 400 may be modified to allow pulsatile or continuous and unimpeded movement of the plunger rod within the barrel. In one or more embodiments, the upper portion 410 and the lower portion 412, when attached to the barrel, may be positioned such that cross-sectional width of the full opening 432 at the bottom ends 418 of the upper portion 410 and the lower portion 412 is greater than the cross-sectional width of the fully opening 432 at the joins of the upper portion 410 and the bottom portion 412. In other words, the upper portion 410 may be positioned at a distance from the lower portion 412 to add a space between the bottom portion 418 of each respective portion to increase the cross-sectional width of the full opening 432. In one or more alternative embodiments, the partial opening 430 of at least one of the upper portion 410 or the lower portion 412 may include an inwardly extending notch (not shown) that may allow the protrusions 545 of the plunger rod to slide distally past the first pulsing element 400. Both the upper portion 410 and the lower portion 412 may include a notch if the plunger rod includes protrusions 545 on opposite ends of the body portion 532. In such embodiments, the full opening 432 may be circular and may have a constant cross-sectional width, with an enlarged cross-sectional width at the notch. When the constant cross-sectional width of the full opening 432 is aligned with the protrusions 545, the first pulsing element 400 interacts or engages with the protrusions 545 to provide pulsatile movement of the plunger rod. When the notch or notches in the upper portion 410 and/or the lower portion 412 are aligned with the protrusions 545, the enlarged cross-sectional width of the full opening 432 at the notch permits the plunger rod to move distally past the first pulsing element 400 without interaction or engagement with the first pulsing element to provide continuous and unimpeded movement of the plunger rod. In another variant, the partial opening 430 of at least one of the upper portion 410 or the lower portion 412 may include an outwardly extending notch (not shown) that cooperates with a plunger rod having a plurality of indentations (not shown) disposed along its body portion. Both the upper portion 410 and the lower portion 412 may include an outwardly extending notch if the plunger rod includes a plurality of indentations on opposite ends of the body portion. The cross-sectional width of the plunger rod body measured at the plurality of indentations may be less than the cross-sectional width of the plunger rod body at other locations that do not include any indentations. The outwardly extending notch (not shown) would interact and engage with the portions of the plunger rod that do not include a plurality of indentations to provide pulsatile movement to the plunger rod. The plunger rod and/or the first pulsing element 400 may be rotated to align the outwardly extending notch with the plurality of indentations allow the protrusions 545 of the plunger rod such that the plurality of indentations allow the plunger rod to slide distally past the first pulsing element. In such embodiments, the full opening 432 may be circular and may have a constant cross-sectional width, with a narrowed cross-sectional width at the outwardly extending notch. When the narrowed cross-sectional width of the full opening is aligned with the portions of the plunger rod that are free of any indentations, the first pulsing element interacts or engages with the plunger rod to provide pulsatile movement of the plunger rod. When the outwardly extending notch or notches in the upper portion 410 and/or the lower portion 412 are aligned with the plurality of indentations on the, the narrowed cross-sectional width of the plunger rod at the plurality of indentations accommodates the outwardly extending notch and permits the plunger rod to move distally past the first pulsing element without interaction or engagement with the first pulsing element to provide continuous and unimpeded movement of the plunger rod.

One or more embodiments may include a second pulsing element 600 that may be provided as a separate component for use with a syringe barrel. In such embodiments, the separate one or more pulsing element may be utilized with standard syringe barrel that do not include any features for providing pulsatile movement with the plunger rods described herein or otherwise. Such syringe barrels may be free of any internal projections, such as the retaining ring 345 described above.

FIGS. 29-33 illustrate a second pulsing element 600 that may be disposed adjacent to an open proximal end of a syringe barrel. Specifically, second pulsing element 600 includes a rotatable body 610 having an open distal end, an open proximal end, and an opening 612 therethrough. The second pulsing element 600 is shown with plunger rod 530 shown in FIGS. 17-28 and with an exemplary syringe barrel 620 that is free of any pulsing elements. The syringe barrel 620 includes an open proximal end 621, a distal end 629, and a side wall 622 that extends from the distal end 629 to the proximal end 621. The side wall 622 includes an inside surface 624 that defines a chamber 626 for retaining fluid. The distal end 629 includes a distal wall 628 with a tip 625 extending distally therefrom. The tip 625 includes a passageway 627 therethrough in fluid communication with the chamber 626 and includes a tip cap 623 attached thereto. The open proximal end 621 includes finger flanges 630. The side wall 622 of the barrel may be cylindrical or may have another shape and is free of any features that project into the chamber. The open proximal end 621 includes an attachment feature for attaching the second pulsing element to the open proximal end 621 of the syringe barrel.

When the rotatable body 610 is attached to the open proximal end 621 of the syringe barrel so it is positioned perpendicular to the side wall 622 of the syringe barrel or is parallel to the finger flanges 630. The rotatable body 610 may include a distally extending attachment portion (not shown) for attaching the rotatable body 610 to the proximal end of a syringe barrel. For example, the distally extending attachment portion may form a friction interference fit with the inside surface of the barrel at its open proximal end. Other features for attaching the rotatable body 610 may be utilized, however, such features should not interference with the ability of the rotatable body 610 to rotate. The opening 612 has an oval shape and includes a first point 614 and second point 615 that are opposite each other and a third point 616 and a fourth point 617 that are opposite each other. The distance between the first point 614 and the second point 615 is greater than the distance between the third point 616 and the fourth point 617. The cross-sectional width of the opening 612 measured from the third point 616 to the fourth point 617 is the narrowed cross-sectional width portion 645. The cross-sectional width of the opening 612 measured from the first point 614 to the second point 615 is the enlarged cross-sectional width portion 650. The rotatably body 610 may have a shape that imitates the shape of the opening 612. Accordingly, the position of the rotatable body 610 indicates the position of the opening 612 with respect to the plunger rod, as will be discussed in greater detail below.

Figure 28:
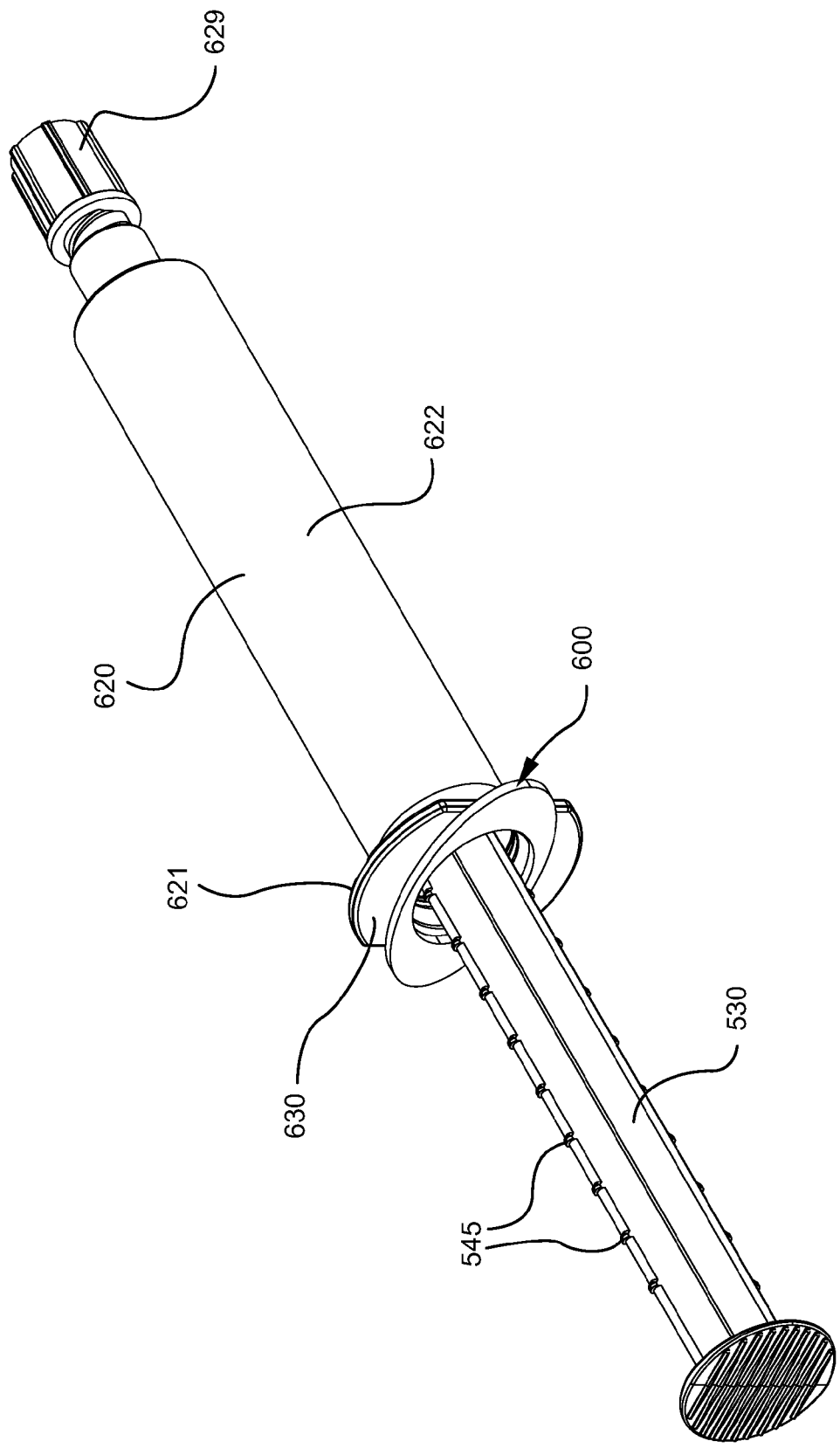
FIG. 28 illustrates a perspective view of a second pulsing element and a flush syringe assembly according to one or more embodiments.
Figure 31:
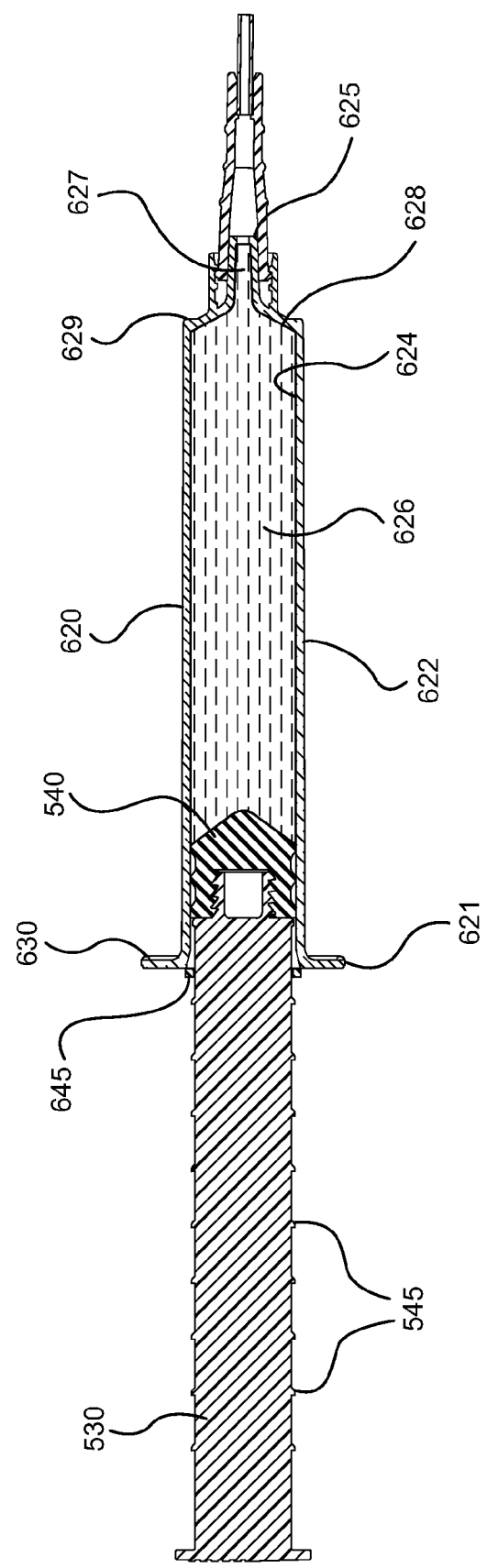
FIG. 31 illustrates a cross-sectional view of the second pulsing element and the flush syringe assembly of FIG. 28.
Figure 32:
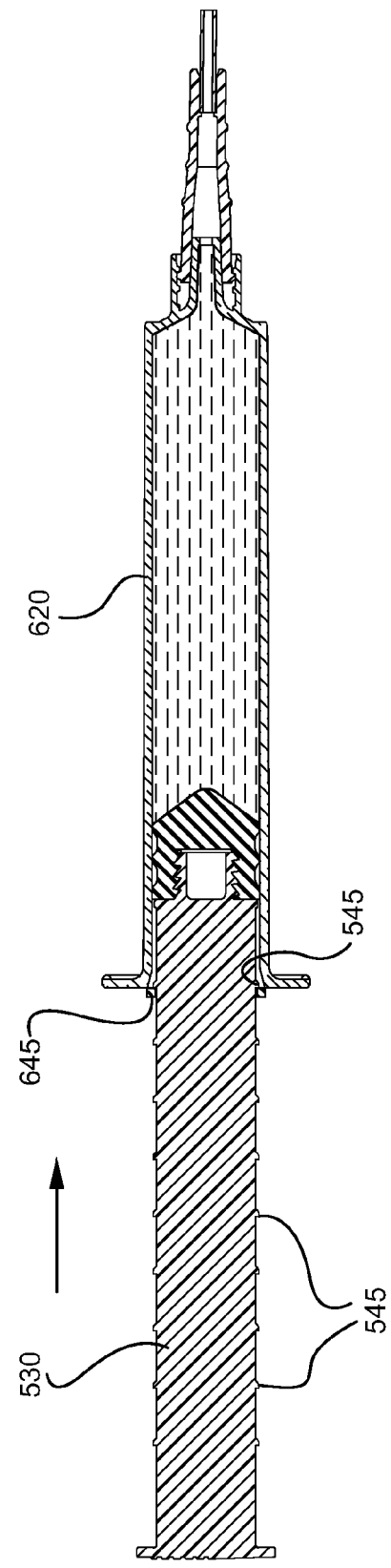
FIG. 32 illustrates the cross-sectional view of the second pulsing element and the flush syringe assembly of FIG. 31 after application of a force in the distal direction on the plunger rod.
Figure 33:
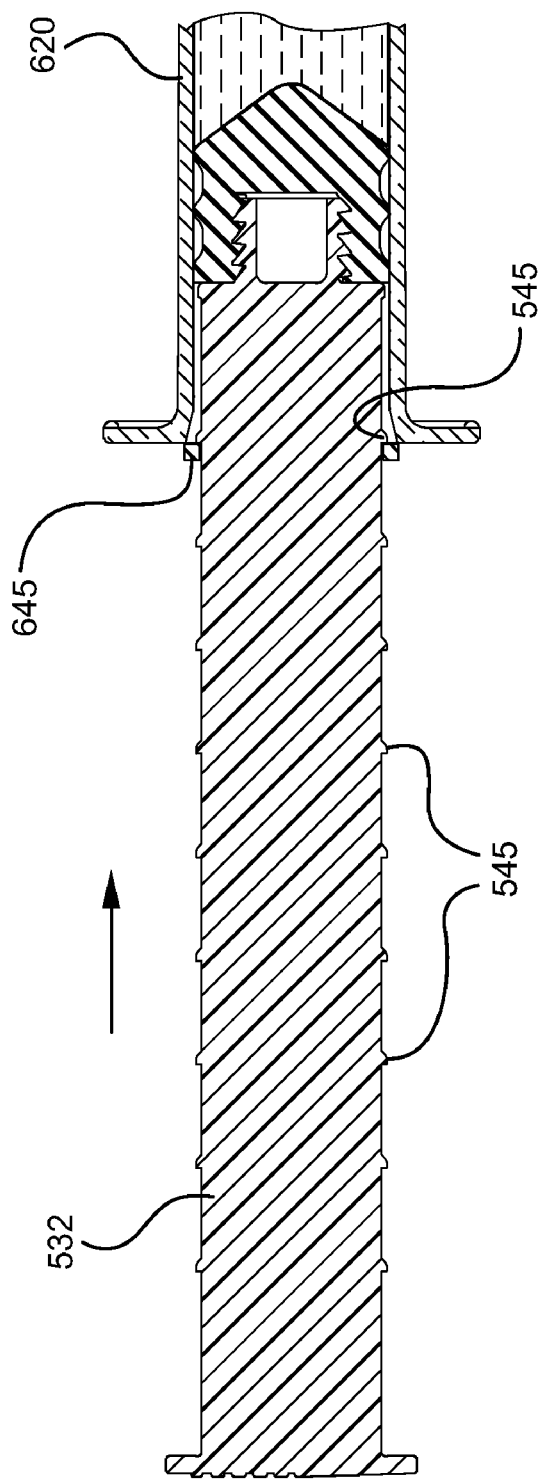
FIG. 33 illustrates an enlarged view of the second pulsing element and the flush syringe assembly of FIG. 32.

In use, the plunger rod 530 is inserted into the chamber 626 through the opening 612 of the rotatable ring. The rotatable ring may be positioned in a pulsing position, as shown in FIG. 28, with the protrusions 545 of plunger rod 530 aligned with the narrowed cross-sectional width portion 645. In this configuration, the interactions between the narrowed cross-sectional width portion 645 and the protrusions 545 will provide pulsatile movement to the plunger rod as it moves within the barrel in the distal direction. In this position, as shown in FIG. 28, the rotatable body 610 is positioned at a 90° angle with respect to the finger flange. This position may function as visual indication that the plunger rod 530 and the second pulsing element 600 are positioned in a pulsing position. The rotatable body 610 may be rotated so it is positioned in a non-pulsing in which the protrusions 545 are aligned with the enlarged cross-sectional width portion 645, as shown in FIG. 31. In this configuration, there would be no interactions between the enlarged cross-sectional width portion 645 and the protrusions 545 will provide pulsatile movement to the plunger rod as it moves within the barrel in the distal direction. In this position, the rotatable body 610 is positioned in alignment with the finger flange. This position may function as visual indication that the plunger rod 530 and the second pulsing element are positioned in a non-pulsing position.

In one or more embodiments, the plunger rod is rotatably disposed within the barrel or, in other words, is disposed within the barrel such that it is able to rotate. As discussed above, the shape of the plunger rod and/or barrel can be modified to allow rotation of the plunger rod when disposed at least partially within the barrel. The amount of rotation may also be limited by modifying the shape of either the plunger rod and/or the barrel. Rotation of the plunger rod within the barrel permits the user to select either pulsatile movement or continuous and unimpeded movement for the movement of the plunger rod within the barrel. In the embodiment shown in FIGS. 9-10, the plunger rod 130 is rotated 90° to switching between pulsatile movement and continuous and unimpeded movement by aligning the discs 145 with the opening of the retaining ring 345 or the portion of the inside surface of the barrel that is free of any elements. Alternatively, the user can rotate the plunger rod 130 by 90° to align the portion of the plunger rod that is free of discs 150 with the retaining ring 345, as shown more clearly in FIGS. 13-14. One of ordinary skill in the art would recognize that the degree of rotation is dependent on the number, size and location of elements utilized on the plunger rod and/or syringe barrel. For example, where one disc is disposed in one quadrant of the plunger rod at one or more location along the axial length of the plunger rod, the user may need to rotate the plunger rod up to 90°.

The alternative embodiment of the plunger rod 230 (shown in FIGS. 4-6) having two protrusions disposed on opposite ends of one beam is shown inserted into the barrel in FIGS. 11-12. The plunger rod 230 must be rotated 90° to align the protrusions 245 with the opening of the retaining ring 350 or the portion of the inside surface of the barrel that is free of any elements. Alternatively, the user can rotate the plunger rod 230 by 90° to align the portion of the plunger rod 250 that is free of protrusions with the retaining ring 345, as shown more clearly in FIGS. 15-16.

Figure 26:
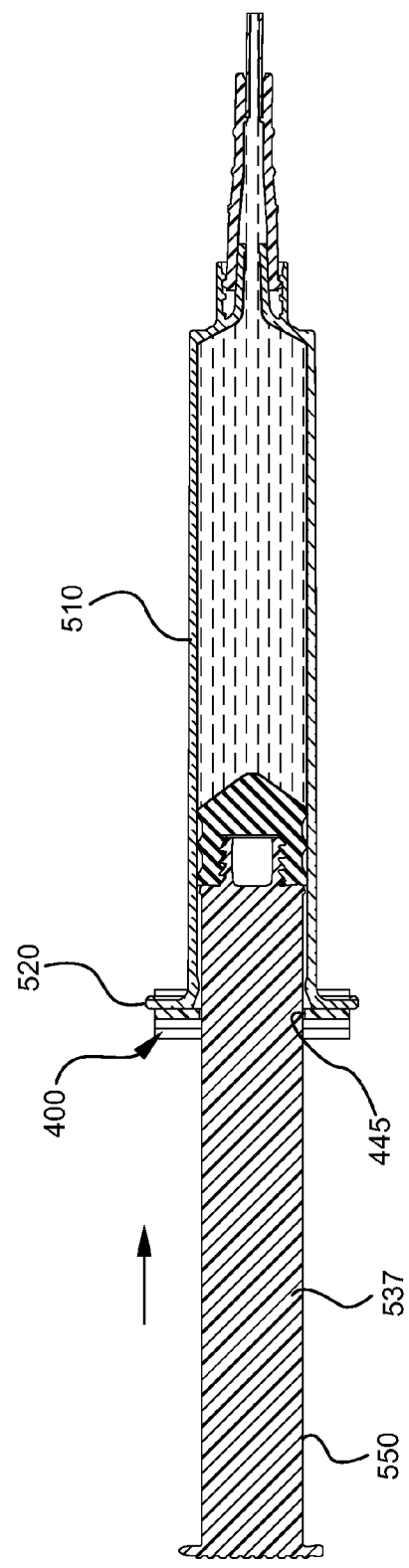
FIG. 26 illustrates a cross-sectional view of the first pulsing element and the flush syringe assembly shown in FIG. 20 after rotating the plunger rod.
Figure 27:
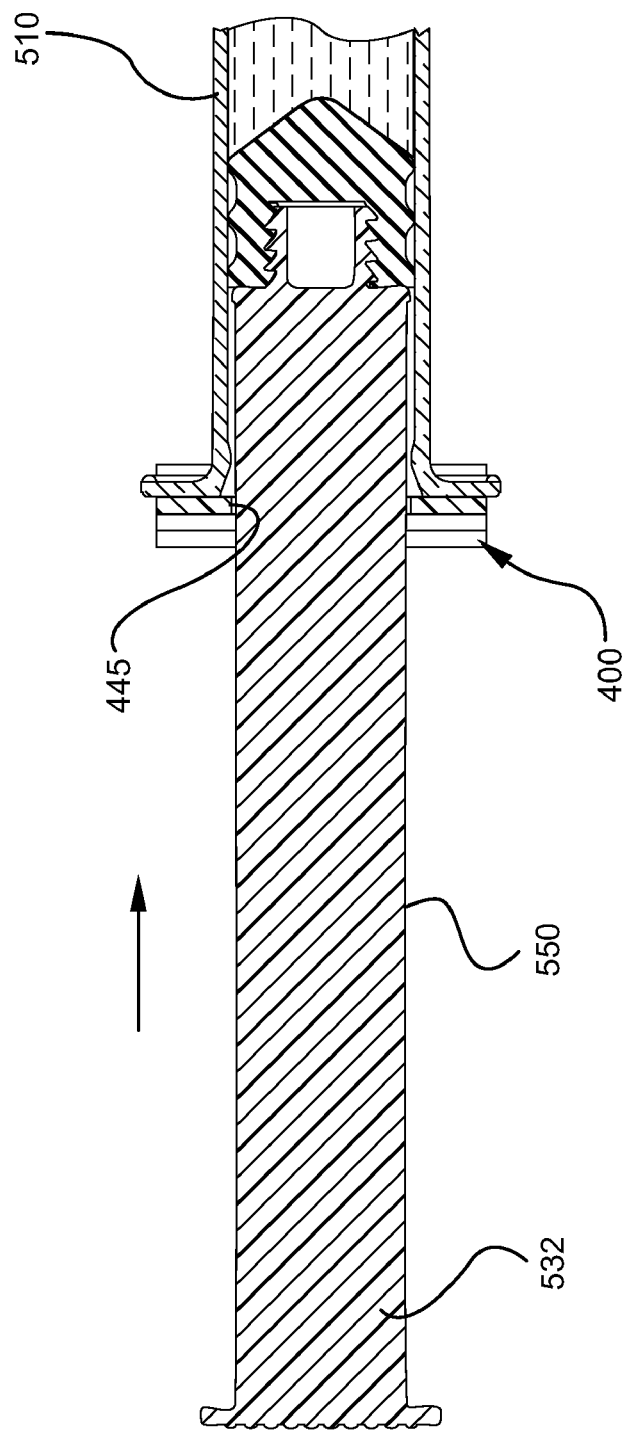
FIG. 27 illustrates an enlarged view of the first pulsing element and flush syringe assembly shown in FIG. 26.

In the embodiment shown in FIGS. 26-27, the plunger rod 530 may be rotated 90° to align the protrusions 545 with the greater cross-sectional width portion 450 of the first pulsing element 400. Alternatively, the user can rotate the plunger rod 530 by 90° to align the portion of the plunger rod 550 that is free of protrusions with the smaller cross-sectional width portion 445 of the first pulsing element. In the embodiment shown in FIG. 28, the plunger rod 530 may be rotated 90° to align the protrusions 545 with the enlarged cross-sectional width portion 650 of the second pulsing element 500. Alternatively, the user can rotate the plunger rod 530 by 90° to align the portion of the plunger rod 550 that is free of protrusions with the narrowed cross-sectional width portion 645 of the pulsing element.

Where only one element is disposed along a portion of the perimeter on the outside surface of the plunger rod, switching between pulsatile movement and continuous and unimpeded movement may require even greater rotation. In embodiments utilizing multiple elements disposed along a portion of the perimeter on the outside surface of the plunger rod, it will be understood that less rotation may be required to align the elements of the plunger rod and the portions of the barrel that are free of elements or the elements disposed on the inside surface of the barrel with the portions of the plunger rod that are free of elements for continuous and unimpeded movement.

Figure 7:
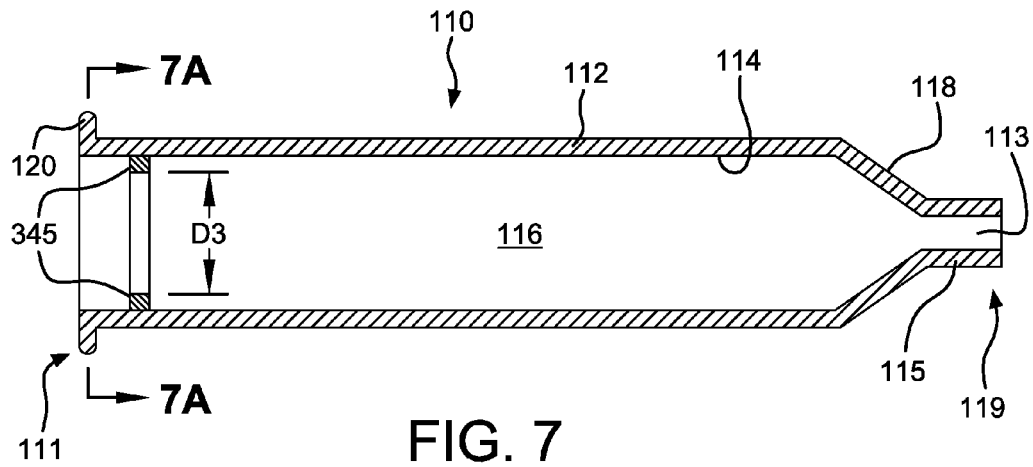
FIG. 7 shows a cross sectional view of a barrel according to an alternative embodiment of the present invention.
Figure 7A:
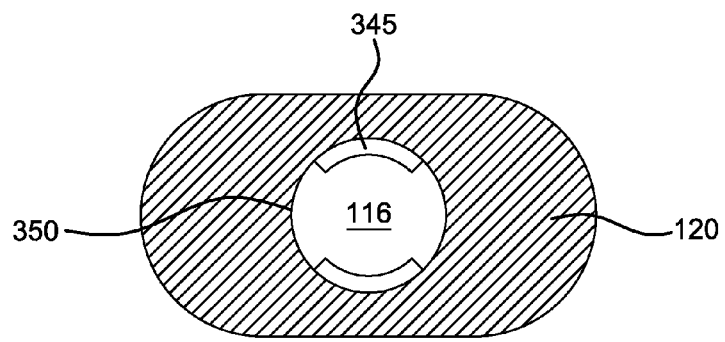
FIG. 7A illustrates a cross-sectional view of the barrel shown in FIG. 7 taken along line 7A-7A.
Figure 8:
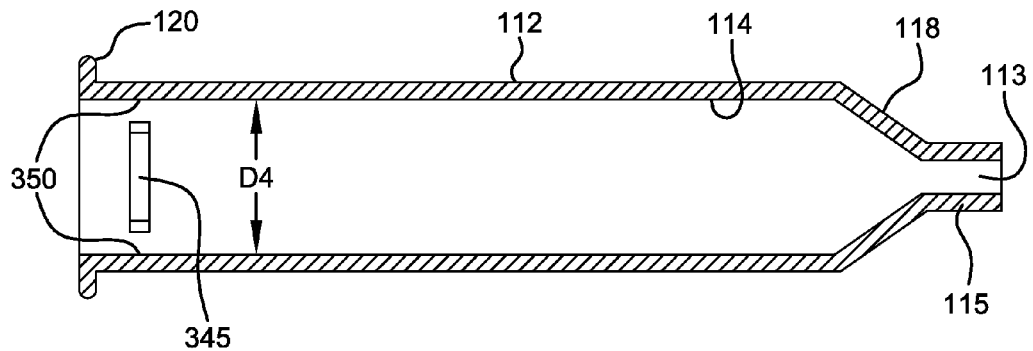
FIG. 8 shows a cross-sectional view of the barrel shown in FIG. 7 rotated 90° clockwise or counterclockwise.

As shown more clearly in FIGS. 3 and 6, the cross-sectional width D1 of the plunger rod measured at a location that includes one or more pulsing elements (for example, at discs 145 and protrusions 245, of FIGS. 3 and 6, respectively) is greater than the cross-sectional width D2 of the plunger rod measured at a location free of any elements. Referring to FIGS. 7 and 8, the cross-sectional width D4 of the inside surface of the barrel measured from the portion of the inside surface that is free of any elements (for example, the retaining ring 350) is less than the cross-sectional width D3 of the inside surface of the barrel measured at the location of the retaining ring 345 disposed on the inside surface of the barrel. When the elements of the plunger rod and barrel are aligned, the larger cross-sectional width of the plunger rod D1 and the decrease cross-sectional width of the barrel D2 create variations in mechanical inference between the plunger rod as it slides distally past the elements disposed on the inside surface of the barrel.

When continuous and unimpeded movement is selected, the elements disposed on the plunger rod (for example, at discs 145 and protrusions 245, of FIGS. 3 and 6, respectively) are aligned with portions of the inside surface of the barrel that are free of any elements (for example, at reference numeral 350 of FIG. 8). In other words, when the elements of the plunger rod are aligned with the portions of the inside surface of the barrel that are free of any elements, the increased cross-sectional width of the inside surface of the barrel D4, permits the increased cross-sectional width of the plunger rod D1 to advance distally without any increase or variation in mechanical interference.

Similarly, when the elements (for example, the retaining ring 350) disposed on the inside surface of the barrel are aligned with the portions of the plunger rod that are free of elements (for example, at reference numeral 150 of FIG. 3, and reference numeral 250 of FIG. 6), continuous and unimpeded movement between the plunger rod and barrel is permitted. In other words, when the elements of the barrel (for example, the retaining ring 350) are aligned with the portions of the plunger rod that are free of elements (for example, the at reference numeral 150 of FIG. 3, and reference numeral 250 of FIG. 6), the decreased cross-sectional width of the plunger rod is permitted to advance distally past the elements of the barrel and within the barrel without any significant or additional changes in mechanical interference between the plunger rod and barrel.

The interaction between the pulsing elements disposed on the plunger rod (i.e., discs 145, protrusions 245 and/or protrusions 545) with the pulsing elements disposed on the barrel or attached as separate pieces on the barrel (i.e., retaining ring 345 smaller cross-sectional width portion 445 and/or the narrowed cross-sectional width portion 645) provides resistance to movement of the plunger rod in the distal direction. As additional mechanical force is applied to the plunger rod to allow the pulsing elements of the plunger rod to overcome the pulsing elements of the barrel, the advancement of the pulsing elements of the plunger rod past the pulsing elements of the barrel causes variations in the interference between the plunger rod and the barrel as the plunger rod moves in the distal direction within the barrel. When the pulsing elements of the plunger rod (i.e., discs 145, protrusions 245 and/or protrusions 545) are no longer aligned with the pulsing elements of the barrel (i.e., retaining ring 345, smaller cross-sectional width portion 445 and the narrowed cross-sectional width portion 645), there is no interaction between the pulsing elements of the plunger rod and the pulsing element of the barrel and, thus, no interactions or variations in the interference between the plunger rod and the barrel.

In one or more embodiments, the plunger rod and/or barrel may include a locking feature that prevents further rotation of the plunger rod, the barrel and/or the rotating body of the barrel when pulsatile or continuous and unimpeded movement is selected. In one or more embodiment, the locking feature may include an increased friction surface (not shown) on the inside surface of the barrel or retaining ring and/or the outside surface of the plunger rod that requires a user to apply a greater force to rotate the plunger rod, barrel and/or rotating body with respect to each other than is normally experienced during normal use of the flush syringe assemblies described herein. In one or more embodiments, the inside surface of the barrel and/or rotating body may include a indented portion (not shown) that receives and holds the one or more pulsing elements disposed on the outside surface of the plunger rod. The indented portion (not shown) would provide an increased cross-sectional width to accommodate the increased cross-sectional width of the plunger rod at the location of the one or more pulsing elements. The indented portion (not shown) would also provide a physical barrier to prevent unintentional rotation that would require the user to apply a greater rotational force on the plunger rod, barrel or rotating body to actively rotate the plunger rod, barrel or rotating body. The rotational force required would be greater than the rotational forces that may occur during normal use of the flush syringe assemblies described herein.

In operation, the syringe assemblies described herein may be connected to a needle assembly and filled with flush solution using known methods. Also, the syringe assembly may be provided pre-filled from the manufacturer or supplier. The flush solution may be any solution intended for flushing or maintaining the performance of VAD's. Exemplary flush solutions include saline flush solution and/or heparin lock flush solution. These solutions are known in the art and readily available. An example of a saline flush solution is 0.9% Sodium Chloride USP for injection. An example of a heparin lock flush solution is 0.9% Sodium Chloride with 100 USP units of Heparin Sodium per ml or 10 USP units of Heparin Sodium per ml. If attached to a needle assembly, the syringe assembly is used to pierce a pierceable septum or a blunt cannula that may be inserted into a pre-split septum of a vial or neck of a glass ampoule containing flush solution and the flush solution is drawn into the syringe barrel by pulling plunger rod in the proximal direction while holding barrel, to draw fluid through the needle cannula into chamber. Alternatively, large quantities of flush syringes may be pre-filled with flush solution during or after the assembly of the syringe using sterile filling methods. Such prefilled syringes may be supplied with a tip cap (not shown) that seals the passageway 113 of the barrel. The tip cap may be is formed of material selected from a group of thermoplastic materials and elastomeric materials such as natural and synthetic rubber, thermoplastic elastomers or combinations thereof. Once assembled, the syringe assembly may be used in flushing a VAD such as a catheter of an I.V. set.

In one or more embodiments, the syringe assemblies described herein may be incorporated into an infusion pump delivery system. As is known in the art, push-pulse flushing techniques are not suitable for use with infusion pump delivery systems, which are typically utilized to provide slow, controlled delivery of flush solution, for example, in pediatric settings. Infusion pump delivery systems incorporate pressure alarms or other instruments to measure increases or changes in pressure or force between the plunger rod and barrel. Accordingly, when push-pulse flushing techniques are used in infusion pump delivery systems, the pressure or force between the plunger rod and barrel changes and may trigger the pressure alarms and other instrumentation. Such alarms may cause the pump delivery system to shut down. The syringe assemblies described herein may be utilized for infusion pump delivery systems and other similar pressure sensitive systems by adjusting the plunger rod and/or barrel to select continuous and unimpeded movement, which replicates a smooth flushing technique, instead of a flushing technique that results in pulsed fluid flow from the syringe such as manual push-pulse and pulsatile flushing techniques described herein.

In accordance with one or more embodiments, the one or pulsing more elements disposed on the plunger rod and/or inside surface of the barrel are shaped to interfere or form enhanced mechanical interference with the syringe barrel during movement of the plunger rod in the distal direction. Changes in mechanical forces between the plunger rod and barrel impede, slow or stop movement of the plunger rod as the user applies a force to the plunger rod in the distal direction during expulsion. As a result, the user must apply a greater force to the plunger rod in the distal direction to advance distally past the elements. The changes in the force applied to the plunger rod forms pulsed movement of the plunger rod, which pulses in fluid flow and imparts the desired turbulent or pulsing flow to the flush solution. The changes in flow rate caused by different forces applied to the plunger rod further increases the turbulence of the flush solution. As the user expels the flush solution from the chamber of the barrel, the increased mechanical interference between the plunger rod and barrel result in undulating forces applied to the plunger rod and forces applied to the flush flow, creating a turbulent or pulsing flow. Without impediments or other features which increase mechanical interference between the barrel and plunger rod, there is no need for the user to change the force applied to the plunger rod and the flush solution is not imparted with turbulent or pulsing flow.

In embodiments utilizing more than one element disposed at different locations along the axial length of the plunger rod or length of the inside surface of the barrel, additional mechanical interference is created after plunger rod has advanced distally past the first element. After advancing distally past the first element at a first location, the user must apply an additional force to the plunger rod when the second element is encountered at a location closer to the distal wall. Multiple changes in the force applied to the plunger rod forms pulsatile movement of the plunger rod, which imparts the desired turbulent or pulsing flow to the flush solution.

In one or more embodiments, the elements disposed on the plunger rod and/or the inside surface of the barrel may be shaped to offer increased resistance at different stages of expulsion of the flush solution. In a specific embodiment, the elements disposed on the plunger rod and/or the inside surface may be positioned at different locations and/or intervals to increase the time between pulses or changes in force applied by the user to the plunger rod in the distal direction.

The flush syringe assemblies described herein may also include visual or other indication elements to indicate the position of the plunger rod, syringe barrel and pulsing elements and thus, indicate whether movement of the plunger rod within the barrel will be pulsatile or continuous and unimpeded. For example, the thumb press may have a color disposed on a portion of the thereon that is aligned with the pulsing elements disposed on the plunger rod, as described herein. The barrel may include corresponding color disposed on the finger flange or other portion of the barrel that is aligned with the pulsing element disposed on the barrel. The first pulsing element 400 and the second pulsing element 600 may also have a color disposed on the portion that is aligned with the smaller cross-sectional portion 445 of the first pulsing element 400 and the narrowed cross-sectional portion 645 of the second pulsing element 600. Accordingly, in use the alignment of the colored portions on the thumb press and the barrel and/or first or second pulsing elements, indicates to the user that the flush syringe assembly is configured for pulsatile movement of the plunger rod within the barrel. Other visual markers may also be utilized, for example, symbols and words may be disposed on the thumb press, barrel and/or pulsing elements.

A third aspect of the present invention pertains to a method of flushing a catheter or removing debris and residue from a catheter. In one embodiment, the method includes attaching a flush syringe assembly to a catheter. The flush syringe assembly may include a barrel including a sidewall having an inside surface defining a chamber that contains a pre-selected amount of flush solution. The flush syringe assembly may also include an elongate plunger rod disposed within the barrel and moveable in the distal and proximal directions within the barrel. The plunger rod includes a distal end and a stopper attached to the distal end. The stopper forms a fluid tight seal with the inside surface of the barrel. The flush syringe assembly may include one or more pulsing elements described herein that are rotatable to create pulsatile movement or continuous and unimpeded movement of the plunger rod within the barrel. The method includes selecting the manner of moving the plunger rod within the barrel. Specifically, the method includes selecting whether to move the plunger rod within the barrel in a pulsatile manner or a continuous and unimpeded manner.

Figure 13:
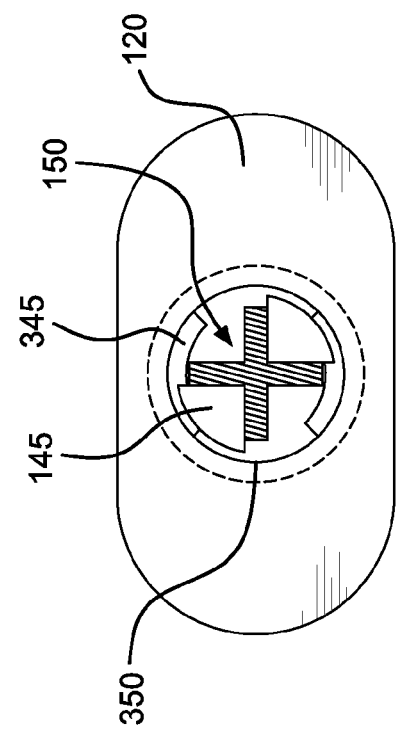
FIG. 13 illustrates a cross-sectional view of FIG. 9 taken along line 13-13.
Figure 14:
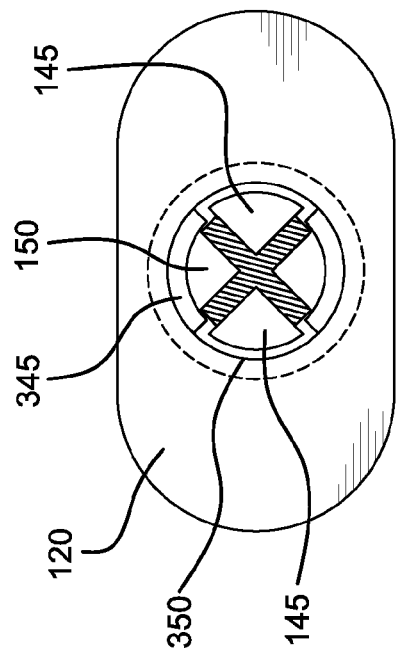
FIG. 14 illustrates a cross-sectional view of FIG. 10 taken along line 14-14.

In the embodiment shown in FIGS. 9 and 10, selecting the manner of moving the plunger rod includes rotating the plunger rod 130. If pulsatile movement is selected, the method includes rotating the plunger rod 130 such that the discs 145 disposed on the plunger rod are aligned with the retaining ring 345. The interaction of the discs 145 and the retaining ring 345 as shown in FIGS. 9 and 13 creates pulsatile movement of the plunger rod because interference between the plunger rod 130 and the barrel 110 is increased. If continuous and unimpeded movement is selected, the method includes rotating the plunger rod 130 such that the discs 145 are not aligned with the retaining ring 345. In this configuration, as shown in FIGS. 10 and 14, there is no interaction between the plunger rod and the barrel and, therefore, there is no change in the interference between the plunger rod 130 and the barrel 110.

Figure 15:
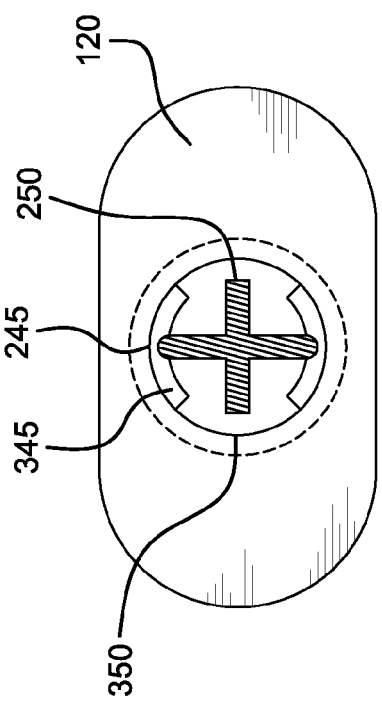
FIG. 15 illustrates a cross-sectional view of FIG. 11 taken along line 15-15.
Figure 16:
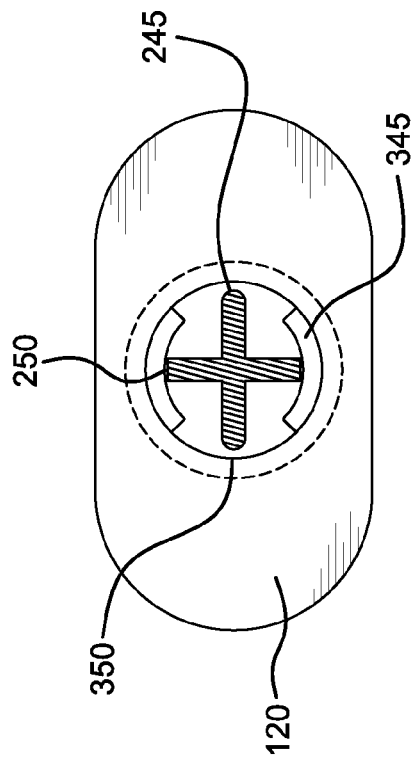
FIG. 16 illustrates a cross-sectional view of FIG. 12 taken along line 16-16.

In the embodiment shown in FIGS. 11 and 12, selecting the manner of moving the plunger rod includes rotating the plunger rod 230. If pulsatile movement is selected, the method includes rotating the plunger rod 230 such that the protrusions 245 disposed on the plunger rod are aligned with the retaining ring 345. The interaction of the protrusions 245 and the retaining ring 345 as shown in FIGS. 11 and 15 creates pulsatile movement of the plunger rod because interference between the plunger rod 230 and the barrel 210 is increased. If continuous and unimpeded movement is selected, the method includes rotating the plunger rod 230 such that the protrusions 245 are not aligned with the retaining ring 345. In this configuration, as shown in FIGS. 12 and 16, there is no interaction between the plunger rod and the barrel and, therefore, there is no change in the interference between the plunger rod 230 and the barrel 210.

In the embodiment shown in FIG. 20, selecting the manner of moving the plunger rod includes rotating the plunger rod 530. If pulsatile movement is selected, the method includes rotating the plunger rod 530 such that the protrusions 545 disposed on the plunger rod are aligned with the smaller cross-sectional portion 445 of the first pulsing element 400. The interaction of the protrusions 545 and the smaller cross-sectional portion 445 creates pulsatile movement of the plunger rod because interference between the plunger rod 530 and the first pulsing element 400 is increased. If continuous and unimpeded movement is selected, the method includes rotating the plunger rod 530 such that the protrusions 545 are not aligned with the smaller cross-sectional portion 445 and are, instead, aligned with the greater cross-sectional portion 450. In this configuration, as shown in FIGS. 26-27, there is no interaction between the plunger rod and the barrel and, therefore, there is no change in the interference between the plunger rod 530 and the first pulsing element 400.

Figure 29:
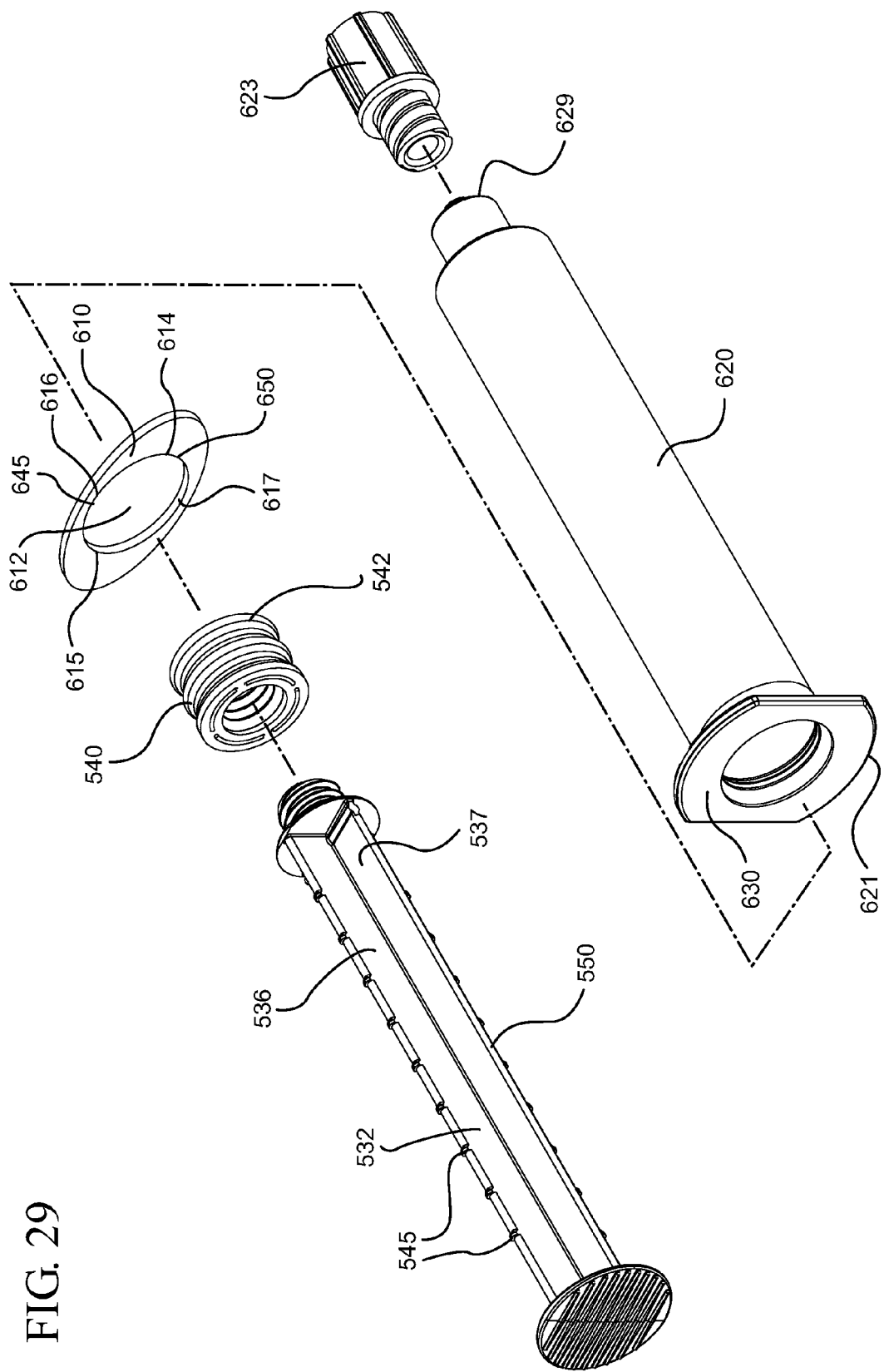
FIG. 29 illustrates an exploded view of the second pulsing element and the flush syringe assembly shown in FIG. 28.
Figure 30:
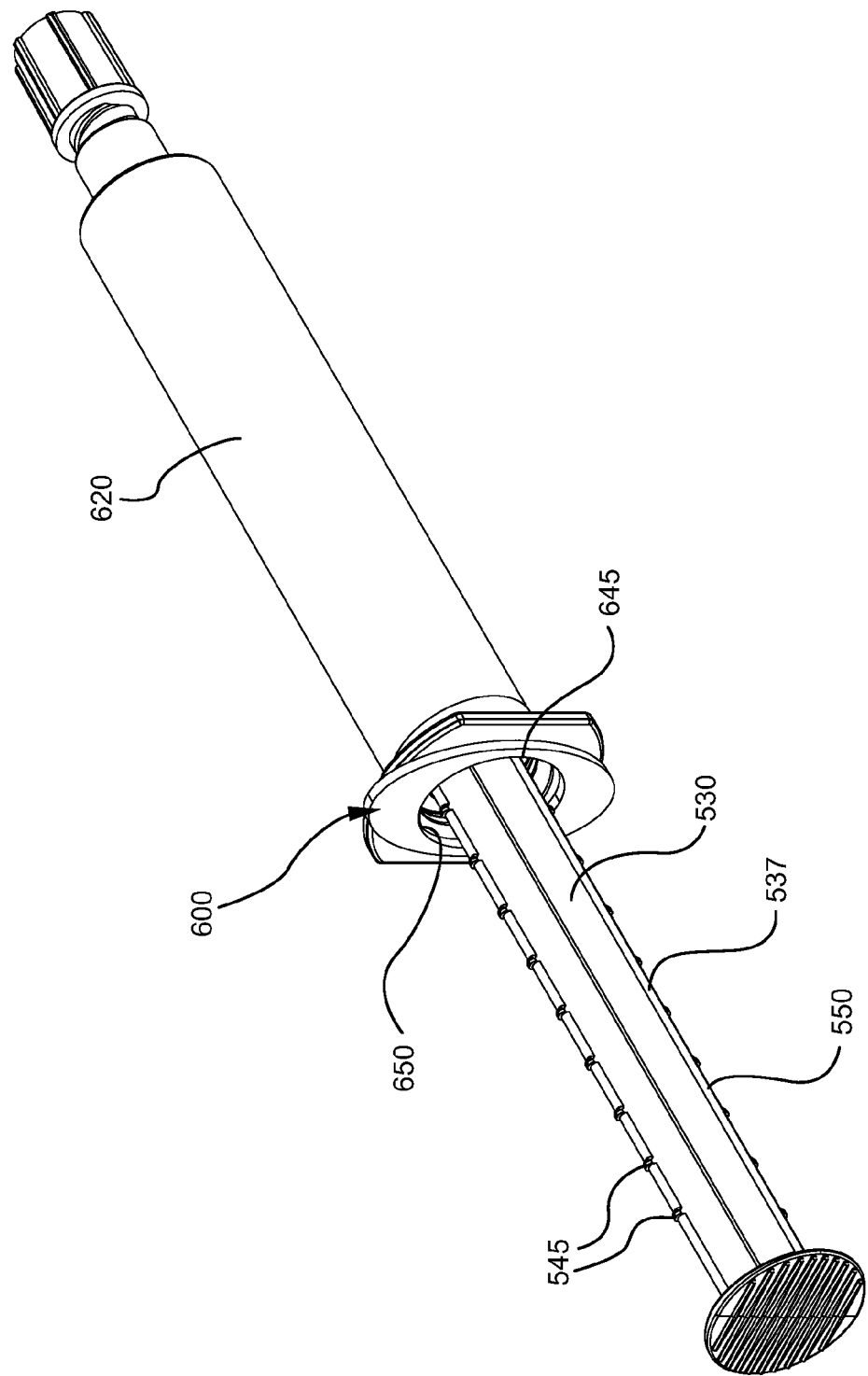
FIG. 30 shows the second pulsing element and the flush syringe assembly shown in FIG. 28 after rotating the second pulsing element.

In the embodiment shown in FIG. 29, selecting the manner of moving the plunger rod includes rotating the rotatable body 610 of the second pulsing element 600. If pulsatile movement is selected, the method includes rotating the rotatable body 610 such that the protrusions 545 disposed on the plunger rod are aligned with the narrowed cross-sectional portion 645 of the first pulsing element 400. The interaction of the protrusions 545 and the narrowed cross-sectional portion 645 creates pulsatile movement of the plunger rod because interference between the plunger rod 530 and the second pulsing element 600 is increased. If continuous and unimpeded movement is selected, the method includes rotating the rotatable body 610 such that the protrusions 545 are not aligned with the narrowed cross-sectional portion 645 and are, instead, aligned with the enlarged cross-sectional portion 650. In this configuration, as shown in FIG. 31, there is no interaction between the plunger rod and the barrel and, therefore, there is no change in the interference between the plunger rod 530 and the second pulsing element 600.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A flush syringe assembly comprising:
   a barrel including a side wall having an inside surface defining a chamber for retaining fluid, an open proximal end and a distal end including a distal wall with a tip extending distally therefrom having a passageway therethrough in fluid communication with said chamber;
   an elongate plunger rod disposed within the barrel, the plunger rod comprising a distal portion and a proximal portion, the plunger rod further comprising a distal end including a stopper having a distal face and a proximal end; and
   one or more pulsing elements disposed on at least one of the plunger rod or the inside surface of the barrel that provide increased mechanical interference between the plunger rod and barrel, the one or more pulsing elements being rotatable to create pulsatile movement or continuous and unimpeded movement of the plunger rod within the barrel.

2. The flush syringe assembly of claim 1, wherein the one or more pulsing elements comprises a plurality of extensions disposed on the outside surface of the plunger rod, the extensions radially outwardly extending toward the inside surface of the barrel.

3. The flush syringe assembly of claim 1, wherein the one or more pulsing elements comprises a plurality of protrusions disposed on the inside surface of the barrel, the protrusions extending radially inwardly toward the outside surface of the plunger rod.

4. The flush syringe assembly of claim 1, wherein the one or more pulsing elements comprise:
  at least one extension disposed on the outside surface of the plunger rod, the extension extending radially outwardly toward the inside surface of the barrel; and
  at least one protrusion disposed on the inside surface of the barrel, the protrusion extending radially inwardly toward the outside surface of the plunger rod, the at least one extension cooperating with the at least one protrusion to increase the interference between the plunger rod and the barrel to require an increased mechanical force to be applied to advance the plunger rod distally into the barrel from the open proximal end of the barrel to the distal wall of the barrel.

5. The flush syringe assembly of claim 4, wherein the one or more pulsing elements comprise a plurality of extensions disposed on the outside surface of the plunger rod and a plurality of protrusions disposed on the inside surface of the barrel.

6. The flush syringe assembly of claim 4, wherein a portion of the outside surface of the plunger rod is free of extensions; and a portion of the inside surface of the barrel is free of protrusions.

7. The flush syringe assembly of claim 4, wherein the plunger rod is rotatable within the barrel to create pulsatile movement or to create continuous and unimpeded movement of the plunger rod within the barrel.

8. The flush syringe assembly of claim 7, wherein movement of the plunger rod in the distal direction creates an interference with the barrel and alignment of the at least one extension and the at least one protrusion results in variations in the interference between the plunger rod and barrel that requires an increase in mechanical force applied to the plunger rod in the distal or proximal direction to overcome the interference.

9. The flush syringe assembly of claim 8, wherein movement of the plunger rod in the distal direction creates an interference with the barrel wherein alignment of the at least one extension disposed on the outside surface of the plunger rod with the portion of the inside surface of the barrel that is free of protrusions results in no variations in the interference between the plunger rod and barrel.

10. The flush syringe assembly of claim 1 wherein the one or more pulsing elements comprise:
  at least one extension disposed on the outside surface of the plunger rod, the extension extending radially outwardly toward the inside surface of the barrel; and
  pulsing element disposed at the proximal end of the barrel, the pulsing element including an inside surface that comprises at least one projection that extends into the chamber, the at least one projection cooperating with the at least one extension on the plunger rod to increase the interference between the plunger rod and the barrel to require an increased mechanical force to be applied to advance the plunger rod distally into the barrel from the open proximal end of the barrel to the distal wall of the barrel.

11. The flush syringe assembly of claim 10, wherein a portion of the outside surface of the plunger rod is free of extensions; and a portion of the inside surface of the pulsing element is free of projections.

12. The flush syringe assembly of claim 11, herein the pulsing element is rotatable with respect to the plunger rod to create pulsatile movement and to create continuous and unimpeded movement of the plunger rod within the barrel.

13. The flush syringe assembly of claim 12, wherein movement of the plunger rod in the distal direction creates an interference with the barrel and alignment of the at least one extension of the plunger rod and the at least one projection of the pulsing element results in variations in the interference between the plunger rod and barrel that require an increase in mechanical force applied to the plunger rod in the distal or proximal direction to overcome the interference.

14. The flush syringe assembly of claim 12, wherein movement of the plunger rod in the distal direction creates an interference with the barrel and alignment of the at least one extension disposed on the outside surface of the plunger rod with the portion of the inside surface of the pulsing element that is free of projections results in no variations in the interference between the plunger rod and barrel.

15. The flush syringe assembly of claim 1, further comprising indicia to provide visual or tactile indication of pulsatile movement of the plunger rod within the barrel.

16. A flush syringe assembly comprising:
  a barrel including a side wall having an inside surface defining a chamber for retaining fluid, an open proximal end and a distal end including a distal wall with a tip extending distally therefrom having a passageway therethrough in fluid communication with said chamber; and
  an elongate plunger rod disposed within the barrel, the plunger rod comprising a distal portion and a proximal portion defining a length, the plunger rod further comprising a distal end including a stopper having a distal face and a proximal end, wherein the barrel and plunger rod are cooperatively configured to permit both pulsatile movement of the plunger rod within the barrel or continuous and unimpeded movement of the plunger rod in the distal direction along substantially the entire length of the barrel upon application of force to the plunger rod in only the distal direction.

17. The flush syringe assembly of claim 16, wherein the plunger rod is rotatably disposed within the barrel to permit selection of pulsatile movement or continuous and uninterrupted movement.

18. The flush syringe of claim 16, wherein a portion of the barrel is rotatable around the plunger rod to permit selection of pulsatile movement or continuous and uninterrupted movement.

19. A method of flushing a catheter comprising:
  attaching a flush syringe assembly to a catheter, the flush syringe assembly comprising a barrel including a side wall having an inside surface defining a chamber containing a preselected amount of flush solution, an elongate plunger rod disposed within the barrel, the plunger rod including a distal end and a stopper attached to the distal end of the plunger rod, and one or more pulsing elements disposed on at least one of the plunger rod or the inside surface of the barrel that provide increase mechanical interference between the plunger rod and barrel, the one or more pulsing elements being rotatable to create pulsatile movement or continuous and unimpeded movement of the plunger rod within the barrel;
selecting the manner of moving the plunger rod within the barrel from one of a pulsatile manner and a continuous and unimpeded manner; and
applying a force in the distal direction to the plunge rod until a desired amount of the flush solution is expelled.

20. The method of claim 19, further comprising changing the manner of moving the plunger rod within the barrel from one of the pulsatile manner and the continuous and unimpeded manner to the other of the pulsatile manner and the continuous and unimpeded manner.

* * * * *